United States Patent [19]

Monkovic et al.

[11] 3,966,747
[45] June 29, 1976

[54] 9-HYDROXY-6,7-BENZOMORPHANS

[75] Inventors: Ivo Monkovic, Candiac; Michel Saucier, Dorval; Yvon Lambert, Cote Ste. Catherine, all of Canada; Thomas Alfred Montzka, Manlius, N.Y.

[73] Assignee: Bristol-Myers Company, New York, N.Y.

[22] Filed: July 9, 1974

[21] Appl. No.: 486,936

Related U.S. Application Data

[63] Continuation-in-part of Ser. No. 301,049, Oct. 26, 1972, abandoned.

[52] U.S. Cl.................. 260/293.54; 260/DIG. 13; 424/267
[51] Int. Cl.² ........................................ C07D 221/26
[58] Field of Search ............... 260/293.54, DIG. 13

[56] References Cited
UNITED STATES PATENTS

| | | | |
|---|---|---|---|
| 3,639,407 | 2/1972 | Clarke et al. | 260/293.54 |
| 3,700,734 | 10/1972 | Robinson et al. | 260/293.54 |
| 3,733,330 | 5/1973 | Schubert et al. | 260/293.54 |

OTHER PUBLICATIONS

May et al., J. Org. Chem. 26, 188, (1961).
May et al., J. Org. Chem. 26, 1621 (1961).
May et al., J. Med. Chem. 8, 235, (1965).
May et al., J. Org. Chem. 26, 1954, (1961).
May et al., J. Org. Chem. 26, 4536, (1961).

*Primary Examiner*—G. Thomas Todd
*Attorney, Agent, or Firm*—Robert E. Havranek

[57] ABSTRACT

N-substituted-9-hydroxy-6,7-benzomorphans have been found to possess potent narcotic agonist and/or antagonist activity. In particular, the compound 2'-hydroxy-2-cyclobutylmethyl-5-allyl-9β-hydroxy-9α-methyl-6,7-benzomorphan has been found to possess potent narcotic agonist and antagonist activity. These compounds are prepared by total synthesis and are not derived from opium alkaloids.

17 Claims, No Drawings

9-HYDROXY-6,7-BENZOMORPHANS

CROSS-REFERENCE TO RELATED APPLICATIONS

This application is a continuation-in-part application of copending application, Ser. No. 301,049, filed Oct. 26, 1972, now abandoned.

BACKGROUND OF THE INVENTION

1. Field of the Invention

This invention embodies new and novel compounds useful as analgesics and/or narcotic antagonists and a new and novel total synthesis for their preparation.

2. Description of the Prior Art

A. Everette May and Hiroshi Kugita, J. Org. Chem. 26, 188 (1961) describe compounds having the formula

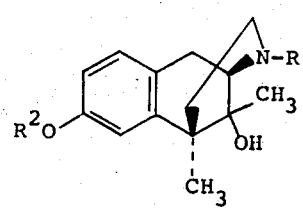

in which $R^2$ is H or methyl and R is methyl or phenethyl as being moderate to weak analgetics.

B. Everette May, James Murphy and J. Harrison Ager, J. Org. Chem. 25, 1386 (1960) report compounds having the formula

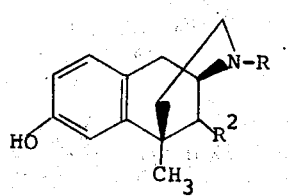

in which R is methyl or phenethyl and $R^2$ is H or methyl as being potent analgetics.

C. Everette May, Hiroshi Kugita and J. Harrison Ager, J. Org. Chem. 26, 1621 (1961) report compounds having the formula

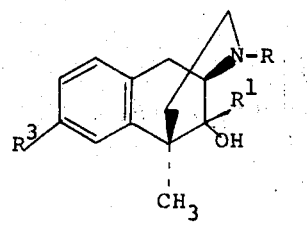

in which R is methyl or phenethyl, $R^1$ is methyl or H, $R^3$ is H, OH or methoxy as producing varying degrees of analgesia.

D. Everette May, Colin Chignell and J. Harrison Ager, J. Med. Chem. 8, 235 (1965) report

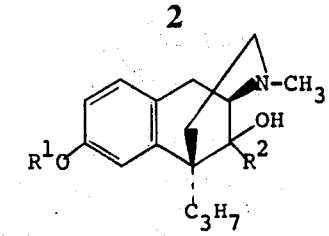

in which $R^1$ is H or methyl and $R^2$ is methyl as possessing analgetic activity.

E. Everette May and Hiroshi Kugita, J. Org. Chem., 26, 1954 (1961) report the compound having the formula

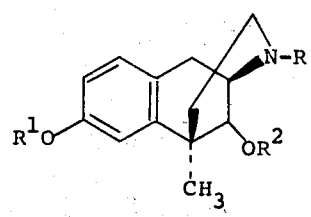

in which R is methyl or phenethyl, $R^1$ is H or methyl and $R^2$ is H or acetyl as having analgetic activity.

F. Everette May and Seiichi Sato, J. Org. Chem. 26, 4536 (1961) report compounds having the formula

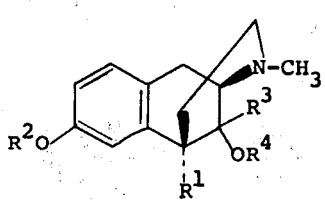

in which $R^2$ is H or methyl, $R^1$ is methyl or ethyl, $R^3$ is methyl or ethyl and $R^4$ is H or acetyl as possessing analgetic activity.

G. N. B. Eddy and E. L. May published a review of 6,7-benzomorphans in Synthetic Analgetics, Pergamon Press (1966).

SUMMARY OF THE INVENTION

Compounds having the formula

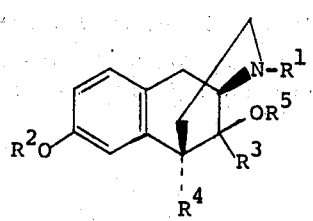  L wherein $R^1$ is selected from the group comprising $-CH_2-C\equiv CH$, $-CH_2-CH=CH_2$,

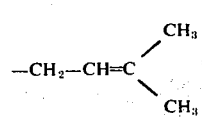

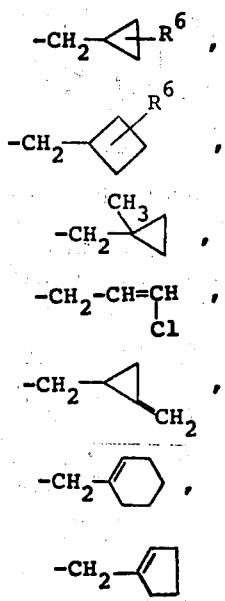

and (lower)alkenyl in which $R^6$ is H or $CH_3$, $R^2$ is selected from the groups comprising H, (lower)alkyl,

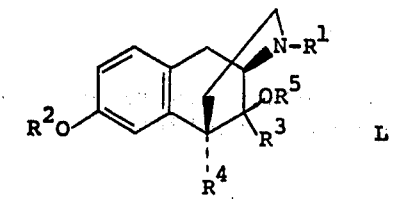

(lower)alkanoyl, and $R^5$ is H, (lower)acyl, trichloroacetyl or cinnamoyl; $R^3$ is H, $CH_3$, $C_2H_5$, $-CH_2-CH=CH_2$ or $-CH_2-C \equiv CH$, $R^4$ is (lower)alkyl, (lower)alkenyl, (lower)-alkynyl or aralkyl; or a pharmaceutically acceptable acid addition salt thereof are analgetic agents, narcotic antagonists or intermediates in the preparation of such agents.

DISCLOSURE OF THE INVENTION

This invention relates to the total synthesis of new and novel N-substituted-9-hydroxy-6,7-benzomorphans having the formula wherein $R^1$ is selected from the group comprising $-CH_2C \equiv CH$, $-CH_2-CH=CH_2$,

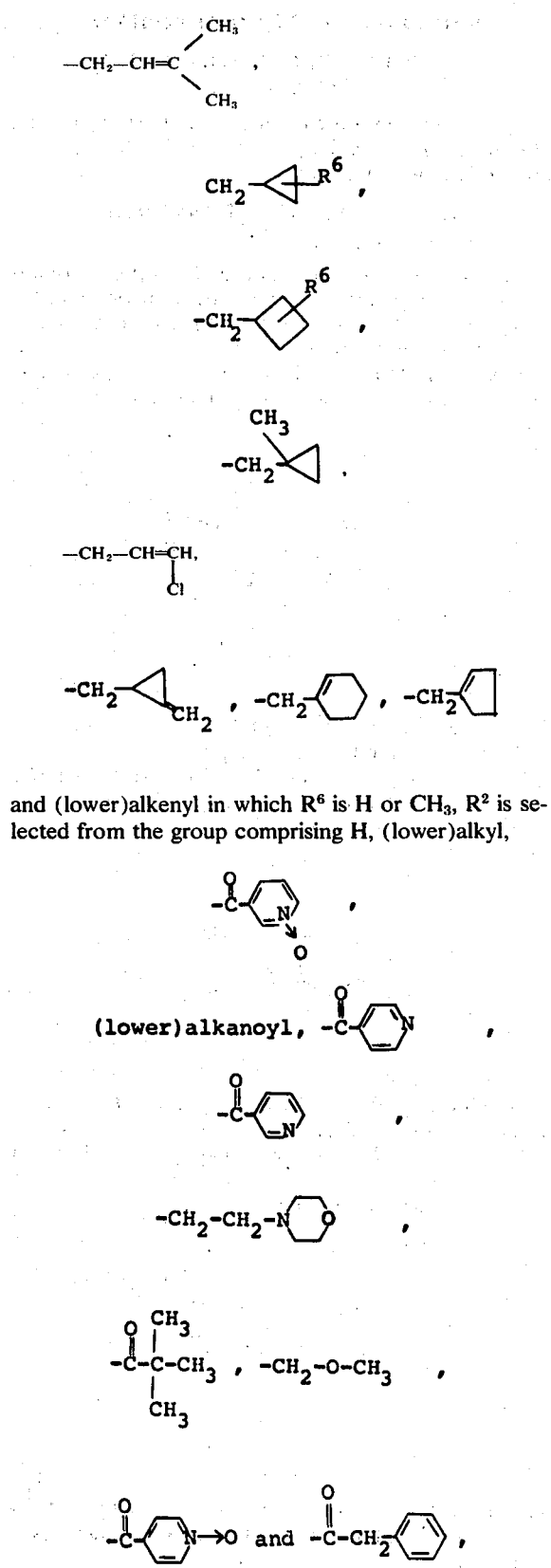

and (lower)alkenyl in which $R^6$ is H or $CH_3$, $R^2$ is selected from the group comprising H, (lower)alkyl, (lower)alkanoyl, and $R^5$ is H, (lower)acyl, trichloroacetyl or cinnamoyl; $R^3$ is H, $CH_3$, $C_2H_5$, $-CH_2-CH=CH_2$ or $-CH_2-C \equiv CH$, $R^4$ is (lower)alkyl, (lower)alkenyl, (lower)alkynyl or aralkyl; or a pharmaceutically acceptable acid addition salt thereof.

Drug abuse by thrill-seeking youth or by people looking for an escape from the realities of every day life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It is therefore an object of the present invention to find new and novel compounds that have these characteristics.

It was further an object of the present invention to develop a method of synthesis that would not be dependent upon alkaloids as starting materials and yet would be commercially feasible.

The objectives of the present invention have been achieved by the provision of the compounds of formula L and by their total synthesis from the readily available starting material 7-methoxy-3,4-dihydro-2[1H]-naphthalenone (I).

The compounds of the instant invention have the basic benzomorphan nucleus which is numbered and represented by the following plane formula

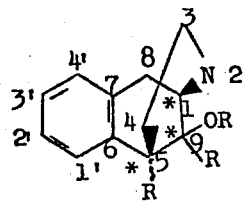

Although there are three asymetric carbons (asterisks) in the benzomorphan molecule, only two diastereoisomeric (racemic) forms are possible, because the iminoethano system, attached to position 1 and 5, is geometrically contained to a cis-(1,3-diaxial)-fusion. These racemates can therefore differ only in the configuration of carbon 9. The only variable will be the cis and trans relationship of the 9-hydroxy compound to the iminoethano system. When in the compounds of the present invention the 9-hydroxy is trans to the iminoethano system, we have the 9α-hydroxybenzomorphans. When the 9-hydroxy is cis to the iminoethano system, we have the 9β-hydroxybenzomorphans.

The use of a graphic representation of a benzomorphan is meant to include the dl racemic mixture and the resolved d and l isomers thereof.

The compounds of the present invention, the 9α and 9β-hydroxybenzomorphans, can exist as two optical isomers, the levorotatory and dextrorotatory isomers. The optical isomers can be graphically illustrated as:

9β-HYDROXYBENZOMORPHAN

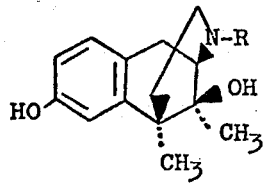

and 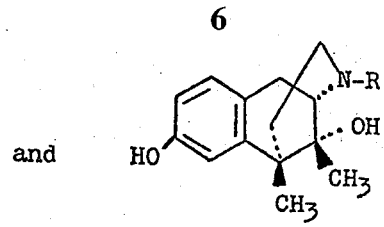

9α-HYDROXYBENZOMORPHAN

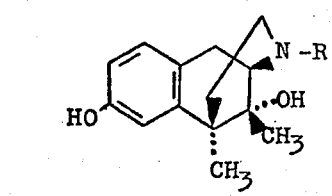

and 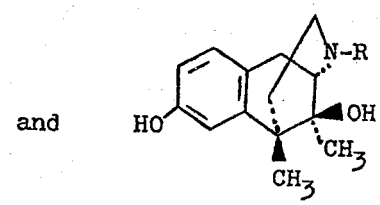

The present invention embodies all of the isomers including the optical isomers in their resolved form.

The optical isomers can be separated and isolated by fractional crystallization of the diastereoisomeric salts formed, for instance, with d- or l- tartaric acid or D-(+)-α-bromocamphor sulfonic acid. The levorotatory isomers of the compounds of the present invention are the most preferred embodiments. Other acids commonly used for resolution can also be employed.

For the purpose of this disclosure, the term "(lower)alkyl" is defined as an alkyl radical containing 1 to 6 carbon atoms. "(Lower)alkenyl" is defined as a hydrocarbon radical of 3 to 7 carbons containing one double bond. The term "(lower)alkanoyl" is a radical of 2 to 6 carbon atoms, e.g., acetyl, propionyl, isobutyryl, etc. the term "pharmaceutically acceptable acid addition salt" is defined to include all those inorganic acid salts of the compounds of the instant invention, which salts are commonly used to produce nontoxic salts of medicinal agents containing amine functions. Illustrative examples would be those salts formed by mixing the compounds of formula L with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, napthalinesulfonic, linoleic or linolenic acid, fumaric, and the like.

Aralkyl for the purpose of this disclosure is a radical having the formula

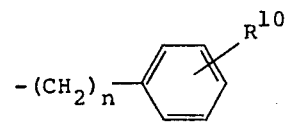

in which n is an integer of 1-6 and $R^{10}$ is H, Cl, Br, F, $NO_2$, (lower)alkyl, (lower)alkoxy or amino, but preferably benzyl or phenethyl.
The compounds of the instant invention are prepared by a total synthesis comprising multiple steps. Surprisingly, the synthesis is efficient and appears commercially feasible. The process is outlined in Charts I through V.
CHART I
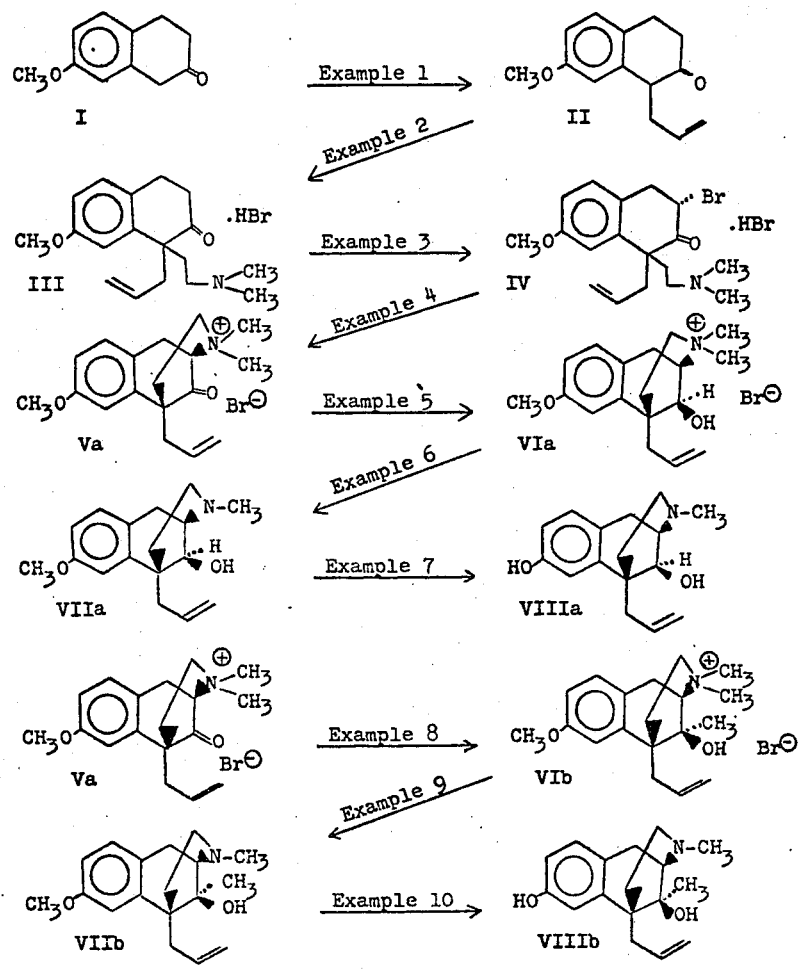
CHART II
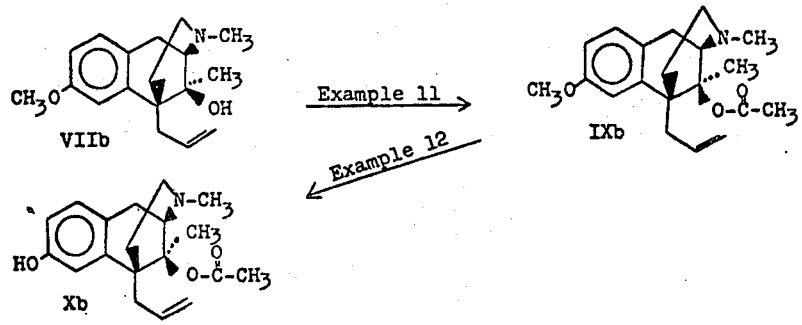

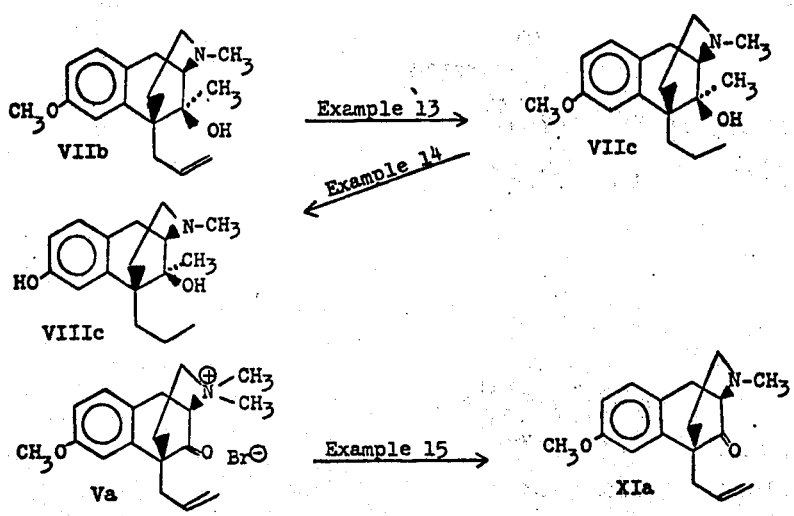
CHART III
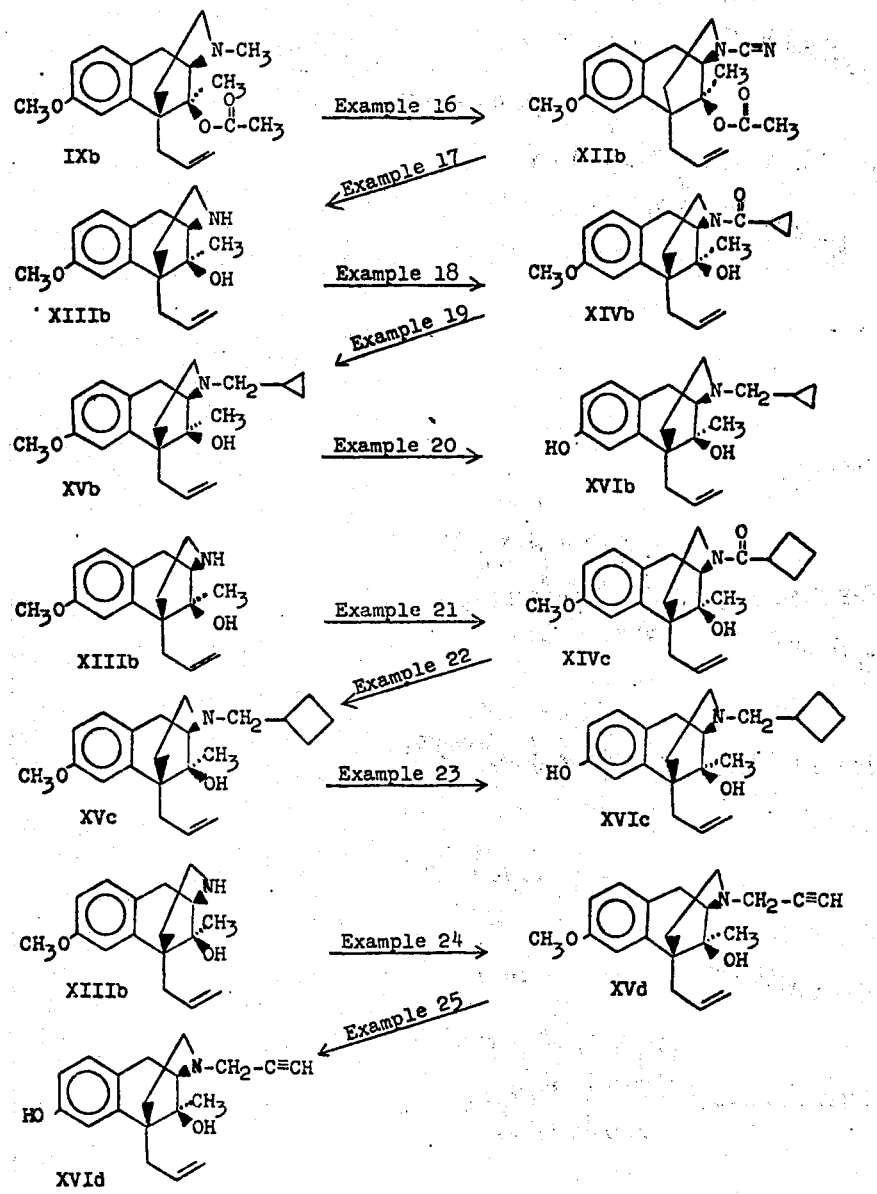

CHART IV
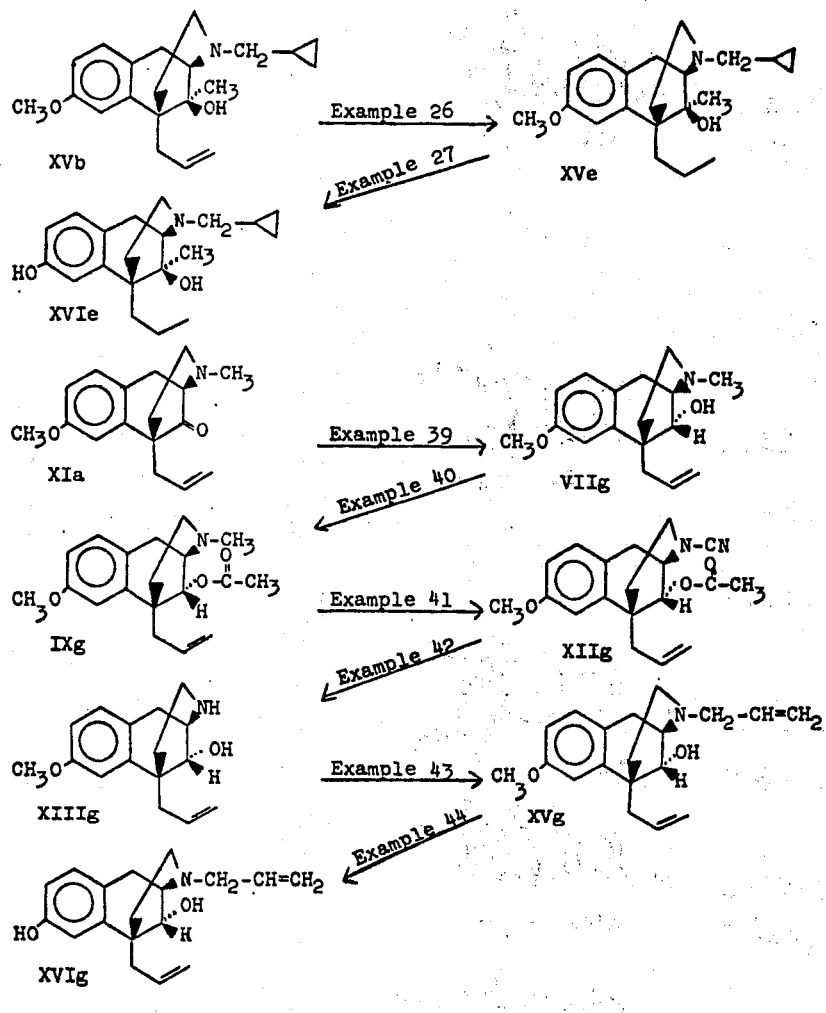
CHART V
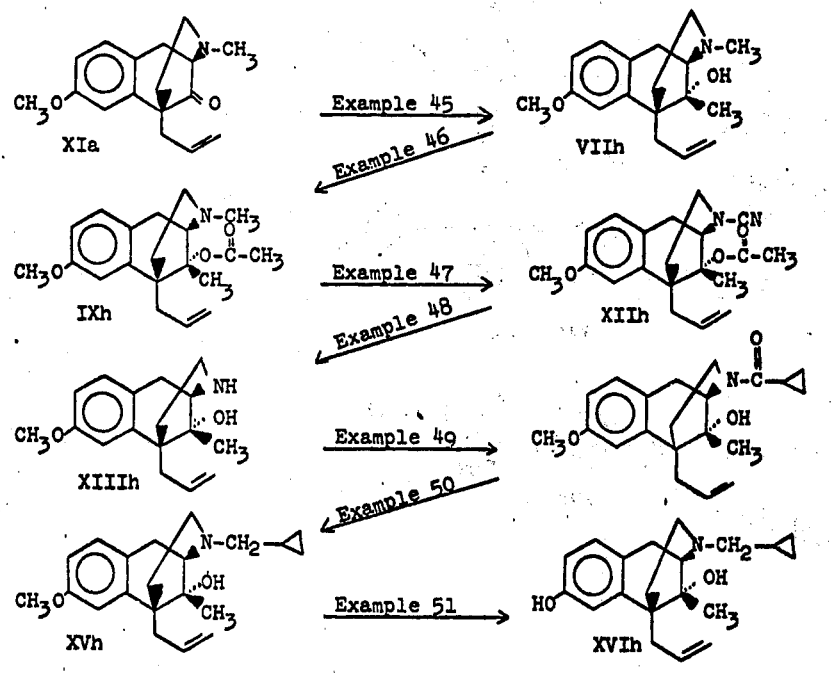

A preferred embodiment of the present invention is the compounds having the formula

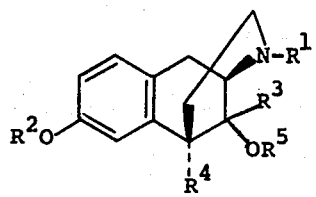   L wherein R¹ is selected from the group comprising

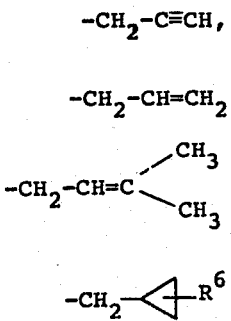

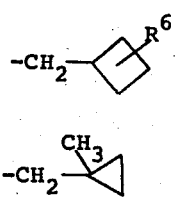

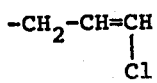

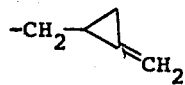

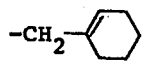

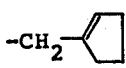

and $C_{3-7}$ alkenyl in which R⁶ is H or $CH_3$; R² is selected from the group comprising H, (lower)alkyl, (lower)alkanoyl,

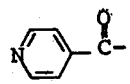

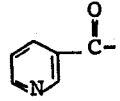

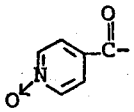

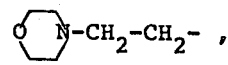

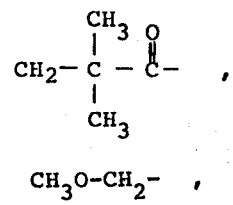

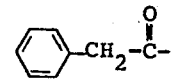

R⁵ is selected from the group comprising H, (lower)acyl, trichloroacetyl and cinnamoyl; R³ is H, $CH_3$, $C_2H_5$, —$CH_2$—CH=$CH_2$ or —$CH_2$—C≡CH; R⁴ is (lower)alkyl, (lower)alkenyl, (lower)alkynyl or aralkyl; or a pharmaceutically acceptable acid addition salt thereof.

Another preferred embodiment is the compounds having the formula

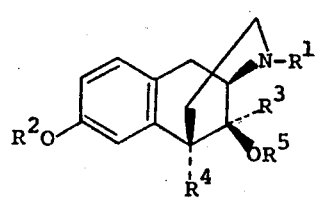   XXXX wherein R¹ is selected from the group comprising —$CH_2$—C≡CH, —$CH_2$—CH=$CH_2$,

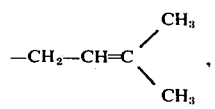

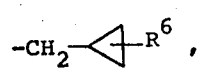

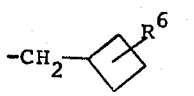

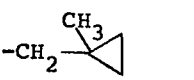

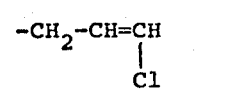

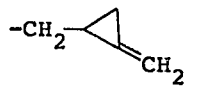

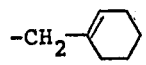

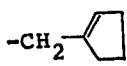

and C$_{3-7}$ alkenyl in which R$^6$ is H or CH$_3$; R$^2$ is selected from the group comprising H, (lower)alkyl, (lower)alkanoyl,

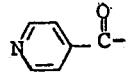

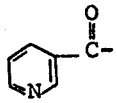

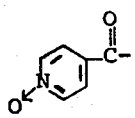

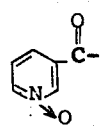

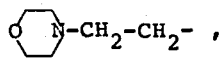

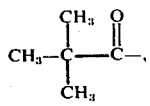

CH$_3$O-CH$_2$- ,

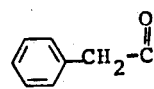

R$^5$ is selected from the group comprising H, (lower)acyl, trichloroacetyl and cinnamoyl; R$^3$ is H, CH$_3$, C$_2$H$_5$, —CH$_2$—CH=CH$_2$, —CH$_2$—C≡CH; R$^4$ is (lower)alkyl, (lower)alkenyl, (lower)alkynyl or aralkyl; or a pharmaceutically acceptable acid addition salt thereof.

A more preferred embodiment is the compounds of formula XXXX wherein R$^1$ is —CH$_2$—C≡CH, —CH$_2$—CH=CH$_2$,

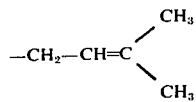

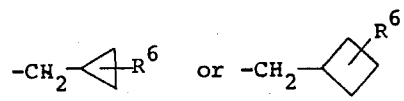

in which R$^6$ is H or CH$_3$, R$^2$ is H, CH$_3$,

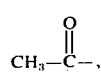

or 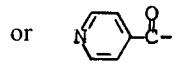

and R$^5$ is H or acetyl, R$^3$ is H, CH$_3$ or C$_2$H$_5$, R$^4$ is (lower)alkyl, (lower)alkenyl or (lower)alkynyl; or a pharmaceutically acceptable acid addition salt thereof.

Another more preferred embodiment is the compounds of formula XXXX wherein R$^1$ is

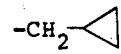

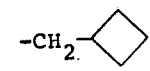

or —CH$_2$—CH=CH$_2$, R$^2$ is H, CH$_3$ or

R$^5$ is hydrogen or acetyl, R$^3$ is methyl, H, R$^4$ is (lower)alkyl or (lower)alkenyl; or a pharmaceutically acceptable acid addition salt thereof.

Another preferred embodiment is the compounds having the formula

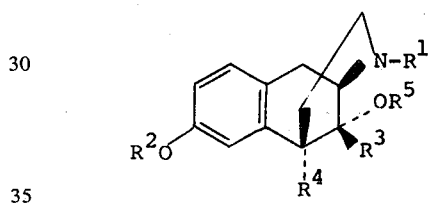

XXXXI wherein R$^1$ is selected from the group comprising —CH$_2$C≡CH, —CH$_2$—CH=CH$_2$,

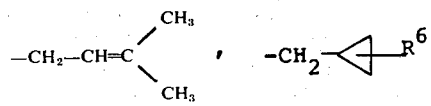

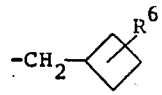

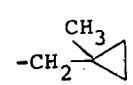

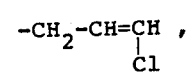

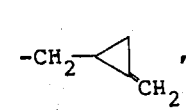

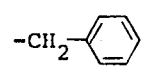

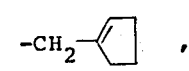

and $C_{3-7}$ alkenyl in which $R^6$ is H or $CH_3$; $R^2$ is selected from the group comprising H, (lower)alkyl, (lower)alkanoyl,

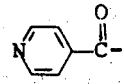

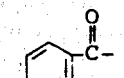

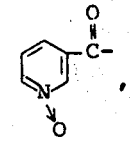

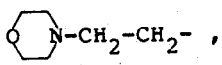

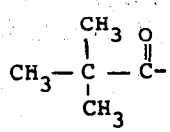

$CH_3O-CH_2-$,

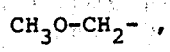

$R^5$ is selected from the group comprising H and (lower)acyl; $R^3$ is H, $CH_3$, $C_2H_5$, $-CH_2-C\equiv CH$; $R^4$ is (lower)alkyl, (lower)alkenyl, (lower)alkynyl or aralkyl; or a pharmaceutically acceptable acid addition salt thereof.

A more preferred embodiment is the compounds of formula XXXXI wherein $R^1$ is $-CH_2-C\equiv CH$, $-CH_2-CH=CH_2$,

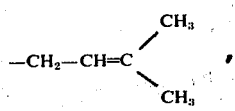

or

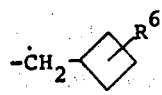

in which $R^6$ is H or $CH_3$, $R^2$ is H, $CH_3$,

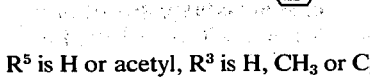

$R^5$ is H or acetyl, $R^3$ is H, $CH_3$ or $C_2H_5$, $R^4$ is (lower)alkyl, (lower)alkenyl or (lower)alkynyl; or a pharmaceutically acceptable acid addition salt thereof.

Another more preferred embodiment is the compounds of formula XXXXI wherein $R^1$ is

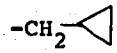

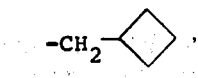

or $-CH_2-CH=CH_2$, $R^2$ is H, $CH_3$ or

$R^5$ is hydrogen or acetyl, $R^3$ is methyl, $R^4$ is (lower)alkyl or (lower)alkenyl; or a pharmaceutically acceptable acid addition salt thereof.

Another more preferred embodiment is the compounds of formula XXXXI wherein $R^1$ is

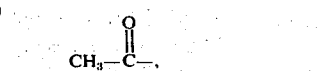

or $-CH_2-CH=CH_2$; $R^2$ is H, $CH_3$, or

$R^5$ is hydrogen, $R^3$ is methyl, $R^4$ is (lower)alkyl or (lower)alkenyl; or a pharmaceutically acceptable acid addition salt thereof.

Most preferred embodiments are:
1. The compounds of formula XXXX wherein $R^1$ is

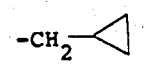

$R^2$ is H, $R^3$ is methyl, $R^4$ is methyl, n-propyl or allyl and $R^5$ is H; or the hydrochloride salt thereof.
2. The compounds of formula XXXX wherein $R^1$ is

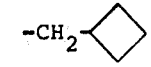

$R^2$ is H, $R^3$ is methyl, $R^4$ is methyl, n-propyl or allyl and $R^5$ is H; or the hydrochloride salt thereof.

3. The compounds of formula XXXX wherein $R^1$ is —$CH_2$—CH=$CH_2$, $R^2$ is H, $R^3$ is methyl, $R^4$ is n-propyl or allyl and $R^5$ is H; or the hydrochloride salt thereof.

4. The compounds of formula XXXX wherein $R^1$ is H, $R^2$ is H or methyl, $R^3$ is H or methyl, $R^4$ is n-propyl or allyl and $R^5$ is H; or an acid addition salt thereof.

5. The compounds of formula XXXXI wherein $R^1$ is

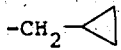

$R^2$ is H, $R^3$ is methyl, $R^4$ is n-propyl or allyl, and $R^5$ is H; or the hydrochloride salt thereof.

6. The compounds of formula XXXXI wherein $R^1$ is

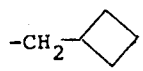

$R^2$ is H, $R^3$ is methyl, $R^4$ is n-propyl or allyl, and $R^5$ is H; or the hydrochloride salt thereof.

7. The compounds of formula XXXXI wherein $R^1$ is —$CH_2$—CH=$CH_2$; $R^2$ is H, $R^3$ is methyl, $R^4$ is n-propyl or allyl, and $R^5$ is H, or the hydrochloride salt thereof.

8. The compounds of formula XXXXI wherein $R^1$ is H; $R^2$ is H or methyl, $R^3$ is H or methyl; $R^4$ is n-propyl or allyl, and $R^5$ is H; or an acid addition salt thereof.

A preferred embodiment of the present invention is the process of preparing compounds having the formula

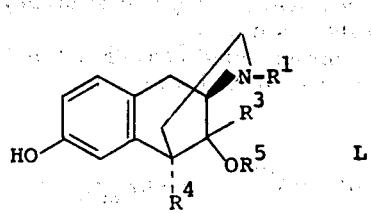

L wherein $R^1$ is selected from the group comprising —$CH_2$—C≡CH, —$CH_2$—CH=$CH_2$,

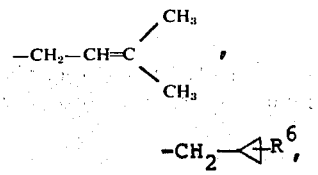

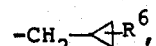

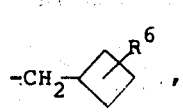

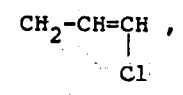

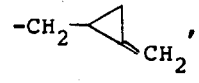

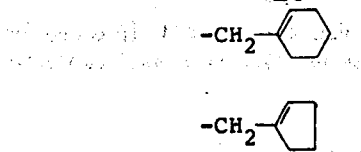

and $C_{3-7}$ alkenyl in which $R^6$ is H or $CH_3$; $R^3$ is H, $CH_3$, $C_2H_5$, —$CH_2$—CH=$CH_2$ or —$CH_2$—C≡CH; $R^4$ is (lower)alkyl, (lower)alkenyl, (lower)alkynyl or aralkyl (benzyl, phenethyl, etc.); $R^5$ is H, (lower)acyl, trifluoroacetyl or cinnamoyl; which process comprises the consecutive steps of A. treating the compound having the formula

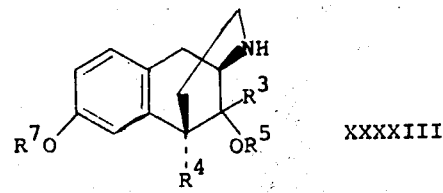 XXXXIII in which $R^7$ is (lower)alkyl, $R^3$, $R^4$ and $R^5$ are as defined above, with an alkylating or acylating agent having the formula

X-(Z)-W in which W is a radical selected from the group comprising —C≡CH, —CH=$CH_2$,

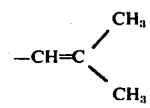

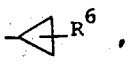

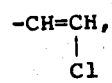

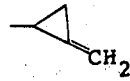

and $C_{2-6}$ alkenyl in which $R^6$ is H or $CH_3$, Z is carbonyl

or —CH$_2$— and X is chloro, bromo or iodo, in an inert organic solvent in the presence of an appropriate base to produce the compound having the formula

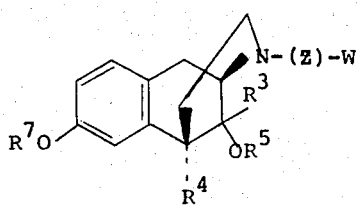
XXXXIV in which R$^7$, R$^3$, R$^4$, R$^5$, Z and W are as defined above;

B. treating compound XXXXIV with lithium aluminum hydride when (Z) is carbonyl

in an inert organic solvent, to produce the compound having the formula

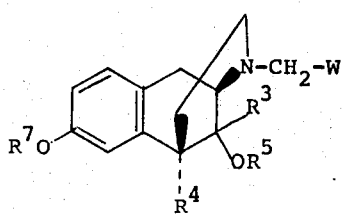
XXXXV in which R$^7$, R$^3$, R$^4$, R$^5$ and W are as defined above; and C. cleaving the phenolic ether function of compound XXXXV by treatment with an agent selected from the group comprising NaS—C$_2$H$_5$, hydrobromic acid, boron tribromide or pyridine hydrochloride.

For the purpose of this disclosure, the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower)alkanols such as methanol, ethanol, n-propanol, isopropanol and the like. The term "appropriate base" includes a tertiary amine commonly employed as a proton acceptor in acylation reactions. Such amines are tri(lower)alkylamines, e.g., trimethylamine, triethylamine, and the like, pyridine, dimethylaniline, N-methylpiperidine, and the like. Other bases are K$_2$CO$_3$, NaHCO$_3$, KOH, NaOH, Na$_2$CO$_3$, and the like.

A preferred embodiment of the present invention is the process of preparing compounds having the formula

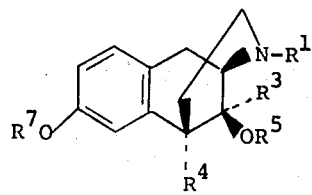
XXXX wherein R$^1$ is selected from the group comprising —CH$_2$—C ≡ CH, —CH$_2$—CH=CH$_2$,

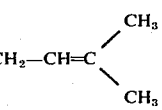

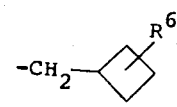

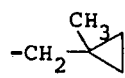

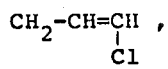

$$CH_2-CH=CH\atop |\ Cl$$ ,

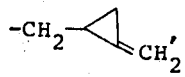

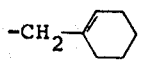

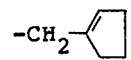

and C$_{3-7}$ alkenyl in which R$^6$ is H or CH$_3$; R$^3$ is H, CH$_3$, C$_2$H$_5$, —CH$_2$—CH=CH$_2$ or —CH$_2$—C ≡ CH; R$^4$ is (lower)alkyl, (lower)alkenyl, (lower)alkynyl or aralkyl (benzyl, phenethyl, etc.); R$^5$ is H, (lower)acyl, trichloroacetyl or cinnamoyl, R$^7$ is H; which process comprises the consecutive steps of A. treating the compound having the formula

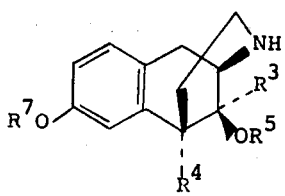
XXXXIII in which R$^7$ is (lower)alkyl, R$^3$, R$^4$ and R$^5$ are as defined above, with an alkylating or acylating agent having the formula

X-(Z)-W in which W is a radical selected from the group comprising —C ≡ CH, —CH=CH$_2$,

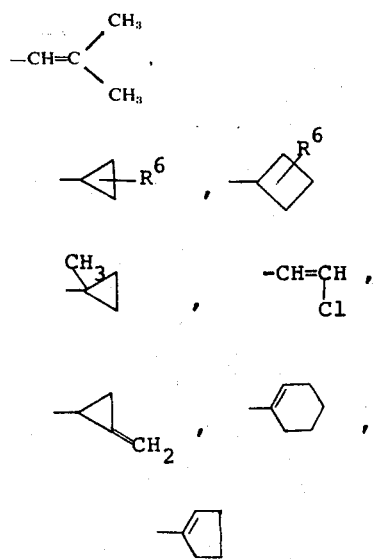

and C$_{2-6}$ alkenyl in which R$^6$ is H or CH$_3$, Z is carbonyl

or —CH$_2$— and X is chloro, bromo or iodo, in an inert organic solvent in the presence of an appropriate base to produce the compound having the formula

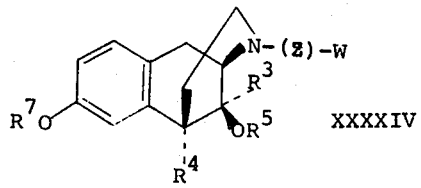      XXXXIV in which R$^7$, R$^3$, R$^4$, R$^5$, Z and W are as defined above;
B. treating compound XXXXIV with lithium aluminum hydride when (Z) is carbonyl

, in an inert organic solvent, to produce the compound having the formula

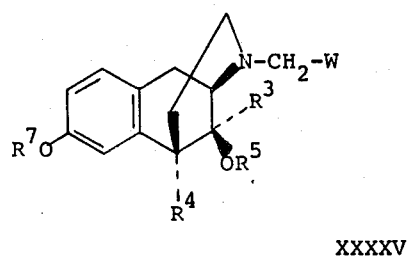

XXXXV in which R$^7$, R$^3$, R$^4$, R$^5$ and W are as defined above; and
C. cleaving the ether function of compound XXXXV by treatment with an agent selected from the group comprising hydrobromic acid, NaS—C$_2$H$_5$, boron tribromide or pyridine hydrochloride.

Another preferred embodiment is the process for preparing compounds having the formula

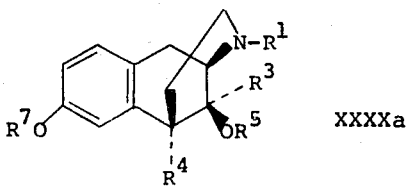      XXXXa wherein R$^1$ is selected from the group comprising —CH$_2$—C ≡ CH,

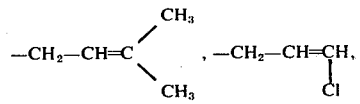

and C$_{3-7}$ alkenyl; R$^3$ is H, CH$_3$, C$_2$H$_5$, —CH$_2$—CH=CH$_2$ or —CH$_2$—C ≡ CH, R$^4$ is (lower)alkyl, (lower)alkenyl, (lower)alkynyl or aralkyl (benzyl, phenethyl, etc.); R$^5$ is H, (lower)acyl, trichloroacetyl or cinnamoyl, R$^7$ is H; which process comprises the consecutive steps of
A. treating the compound having the formula

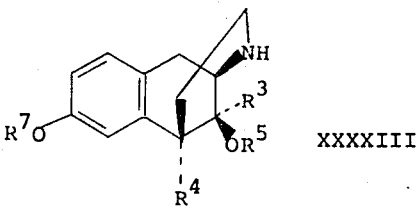      XXXXIII in which R$^7$ is (lower)alkyl and R$^3$, R$^4$ and R$^5$ are as defined above; with an alkylating agent having the formula

R$^1$—X in which R$^1$ is as above and X is chloro, bromo, iodo, in an inert organic solvent in the presence of an appropriate base to produce the compound having the formula

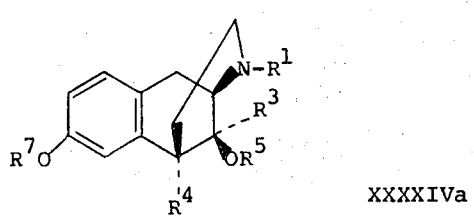

XXXXIVa in which $R^7$, $R^3$, $R^4$, $R^5$ and $R^1$ are as above; and

B. cleaving the ether function of compound XXXXIVa by treatment with NaS—$C_2H_5$, boron tribromide or pyridine hydrochloride.

More preferred embodiments are the process for the preparation of compounds of formula XXXX wherein;

1. In step A $R^7$ is methyl, $R^3$ is H or methyl, $R^4$ is methyl, ethyl, n-propyl, isopropyl, n-butyl, isobutyl, allyl, dimethylallyl or propargyl, $R^5$ is H or acetyl; the inert organic solvent is methylene chloride, dichloroethane or a (lower)alkanol, the base is an alkali metal hydroxide or carbonate and the reaction is conducted at about 15° C. to about reflux temperature.

2. In step A $R^7$ is methyl, $R^3$ is methyl, ethyl, n-propyl, isopropyl, n-butyl, isobutyl, allyl, dimethylallyl or propargyl, $R^5$ is H, the organic solvent is methanol, ethanol, n-propanol or isopropanol, the base is sodium or potassium carbonate and the reaction is conducted at about reflux temperature for about 5 to about 20 hours.

A preferred embodiment of the present invention is the process of preparing compounds having the formula

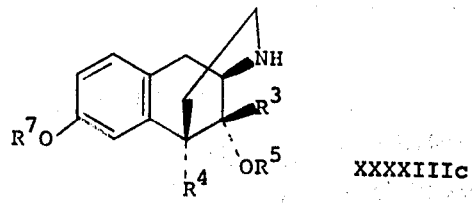

XXXXI wherein $R^1$ is selected from the group comprising —$CH_2$—C ≡ CH, —$CH_2$—CH=$CH_2$,

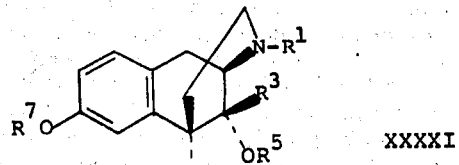

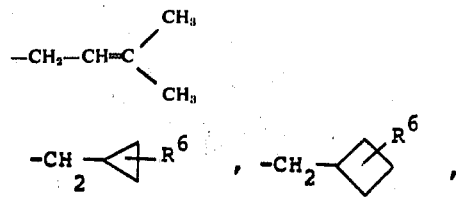

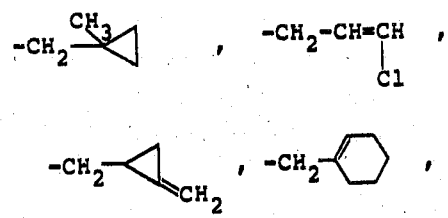

and $C_{3-7}$ alkenyl in which $R^6$ is H or $CH_3$; $R^3$ is H, $CH_3$, $C_2H_5$,

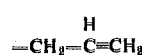

—$CH_2$—C=$CH_2$ 
          |
          H or —$CH_2$—C ≡ CH; $R^4$ is (lower)alkyl, (lower)alkenyl, (lower)alkynyl or aralkyl (benzyl, phenethyl, etc.); $R^5$ is H, (lower)acyl, trichloroacetyl or cinnamoyl, $R^7$ is H; which process comprises the consecutive steps of A. treating the compound having the formula

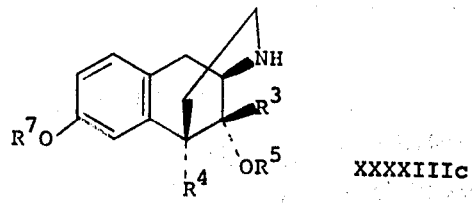

XXXXIIIc in which $R^7$ is (lower)alkyl, $R^3$, $R^4$ and $R^5$ are as defined above, with an alkylating or acylating agent having the formula

X-(Z)-W in which W is a radical selected from the group comprising —C ≡ CH, —CH=$CH_2$,

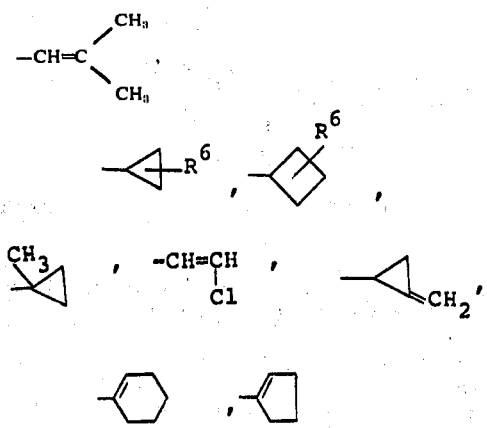

and $C_{2-6}$ alkenyl in which $R^6$ is H or $CH_3$; Z is carbonyl

or —$CH_2$—; and X is chloro, bromo or iodo; in an inert organic solvent in the presence of an appropriate base

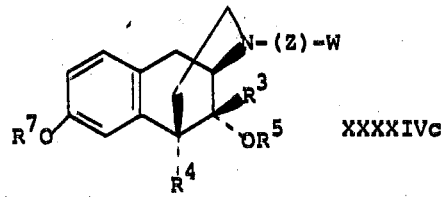

XXXXIVc in which $R^7$, $R^3$, $R^4$, $R^5$, Z and W are as defined above;

B. treating compound XXXXIVc with lithium aluminum hydride when (Z) is carbonyl

in an inert organic solvent, to produce the compound having the formula

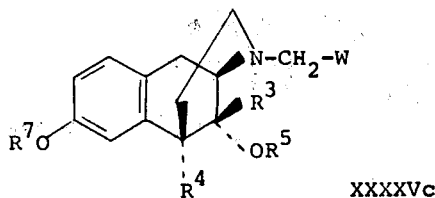

XXXXVc in which $R^7$, $R^3$, $R^4$, $R^5$ and W are as defined above; and

C. cleaving the ether function of compound XXXXVC by treatment with an agent selected from the group comprising $NaS-C_2H_5$, hydrobromic acid, boron tribromide or pyridine hydrochloride.

Another preferred embodiment is the process of preparing compounds having the formula

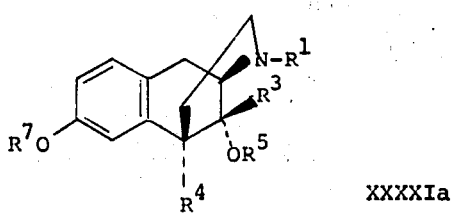

XXXXIa wherein $R^1$ is selected from the group comprising $-CH_2-C\equiv CH$, $-CH_2-CH=CH_2$,

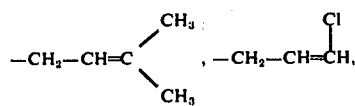

and $C_{3-7}$ alkenyl; $R^3$ is H, $CH_3$, $C_2H_5$, $-CH_2-CH=CH_2$ or $-CH_2-C\equiv CH$, $R^4$ is (lower)alkyl, (lower)alkenyl, (lower)alkynyl or aralkyl (benzyl, phenethyl, etc.); $R^5$ is H, (lower)acyl trifluoroacetyl or cinnamoyl; $R^7$ is H; which process comprises the consecutive steps of A. treating the compound having the formula

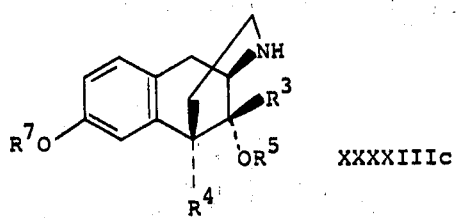

XXXXIIIc in which $R^7$ is (lower)alkyl and $R^3$, $R^4$ and $R^5$ are as defined above; with an alkylating agent having the formula

R-X in which $R^1$ is as above and X is chloro, bromo or iodo, in an inert organic solvent in the presence of an appropriate base to produce the compound having the formula

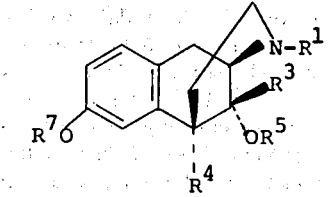

XXXXIVd in which $R^7$, $R^3$, $R^4$, $R^5$ and $R^1$ are as above; and

B. cleaving the ether function of compound XXXXIVd by treatment with $NaS-C_2H_5$, boron tribromide or pyridine hydrochloride.

More preferred embodiments are the process for the preparation of compounds of formula XXXXI wherein:

1. In step A $R^7$ is methyl; $R^3$ is H or methyl; $R^4$ is methyl, ethyl, n-propyl, isopropyl, n-butyl, isobutyl, allyl, dimethylallyl or propargyl, $R^5$ is H or acetyl; the inert organic solvent is methylene chloride, dichloroethane or a (lower)alkanol, the base is an alkali metal hydroxide or carbonate and the reaction is conducted at about 15° C. to about reflux temperature.

2. In step A $R^7$ is methyl, $R^3$ is methyl, $R^4$ is methyl, ethyl, n-propyl, isopropyl, n-butyl, isobutyl, allyl, dimethylallyl or propargyl, $R^5$ is H; the organic solvent is methanol, ethanol, n-propanol or isopropanol, the base is sodium or potassium carbonate and the reaction is conducted at about reflux temperature for about 5 to about 20 hours.

Additional and more preferred embodiments are the following:

1. A compound having the formula

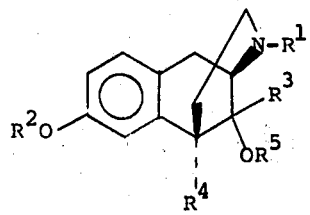

L.

wherein $R^1$ is selected from the group comprising

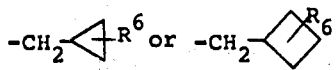

in which $R^6$ is H or $CH_3$, $R^2$ is selected from the group comprising H, (lower)alkyl, (lower)alkanoyl,

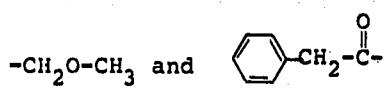

$R^5$ is H, $R^3$ is $CH_3$, $R^4$ is n-propyl, (lower) alkenyl, or a radical having the formula

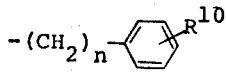

in which n is an integer of 1 to 6 and $R^{10}$ is selected from the group comprising H, Cl, Br, F, $NO_2$, (lower)-alkyl, (lower)alkoxy or amino; or a pharmaceutically acceptable acid addition salt thereof.

2. A compound having the formula

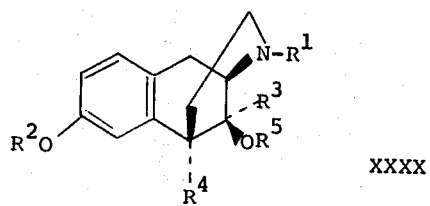

XXXX wherein $R^1$ is selected from the group comprising

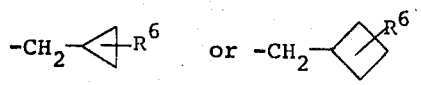

in which $R^6$ is H or $CH_3$, $R^2$ is selected from the group comprising H, (lower)alkyl, (lower)alkanoyl,

—$CH_2O$—$CH_3$ and

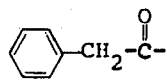

$R^5$ is H, $R^3$ is $CH_3$; $R^4$ is n-propyl, (lower)alkenyl, or a radical having the formula

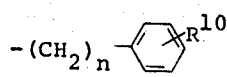

in which n is an integer of 1 to 6 and $R^{10}$ is selected from the group comprising H, Cl, F, Br, $NO_2$, (lower)alkyl, (lower)-alkoxy or amino; or a pharmaceutically acceptable acid addition salt thereof.

3. A compound of formula XXXX wherein $R^1$ is

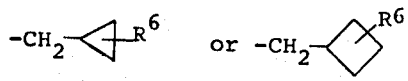

in which $R^6$ is H or $CH_3$, $R^2$ is H, $CH_3$,

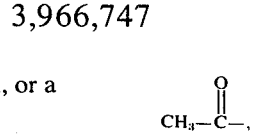

or

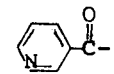

and $R^5$ is H, $R^3$ is $CH_3$, $R^4$ is n-propyl or (lower)alkenyl; or a pharmaceutically acceptable acid addition salt thereof.

4. A compound of formula XXXX wherein $R^1$ is

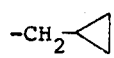 or 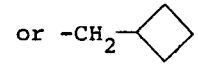

$R^2$ is H, $CH_3$ or

$R^5$ is hydrogen, $R^3$ is methyl, $R^4$ is n-propyl or (lower)alkenyl; or a pharmaceutically acceptable acid addition salt thereof.

5. A compound of formula XXXX wherein $R^1$ is

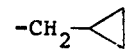

$R^2$ is H, $R^3$ is methyl, $R^4$ is n-propyl or allyl and $R^5$ is H; or the hydrochloride salt thereof.

6. A compound of formula XXXX wherein $R^1$ is

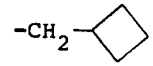

$R^2$ is H, $R^3$ is methyl, $R^4$ is n-propyl or allyl and $R^5$ is H; or the hydrochloride salt thereof.

7. A compound having the formula

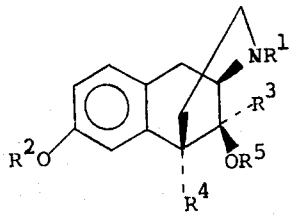

LX wherein $R^1$ is H, $R^2$ is H or (lower)alkyl, $R^3$ is methyl, $R^4$ is n-propyl or allyl, and $R^5$ is H; or an acid addition salt thereof.

8. A compound having the formula

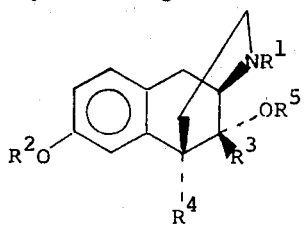

LX wherein $R^1$ is H, $R^2$ is H or (lower)alkyl, $R^3$ is methyl, $R^4$ is n-propyl or allyl, and $R^5$ is H; or an acid addition salt thereof.

9. A compound of formula LX wherein $R^1$ is H, $R^2$ is H or methyl, $R^3$ is methyl, $R^4$ is n-propyl or allyl and $R^5$ is H; or an acid addition salt thereof.

their agonist and/or antagonist properties. Table I represents the results of the experiments. The figures reported are the number of milligrams/ kilogram of body weight of compound that produced an agonist or antagonist effect in 50% of the mice and rats so tested ($ED_{50}$).

TABLE I

| | $ED_{50}$ (mg./kg.)[6] | | | | | | | |
|---|---|---|---|---|---|---|---|---|
| | Agonist Activity Mouse Phenylquinone[1] Writhing | | Antagonist Activity | | | | Morphine Antagonism[4] Rat Tail Flick | |
| | | | Oxymorphone[2] Straub Tail | | Oxymorphone[3] Narcosis | | | |
| Test Compounds | SC | PO | SC | PO | SC | PO | SC | PO |
| dl-XVIc | 0.23 | N.D.[5] | 0.72 | N.D. | 0.30 | N.D. | 0.42 | N.D. |
| l-XVIc | 0.055 | 8 | 0.43 | N.D. | 0.05 | N.D. | 0.08 | 14.1 |
| d-XVIc | >40 | N.D. | ~40 | N.D. | N.D. | N.D. | N.D. | N.D. |
| dl-XVIe | >40 | N.D. | 0.11 | N.D. | 0.08 | N.D. | 0.030 | 6.0 |
| dl-XVId | >40 | N.D. | 1.41 | N.D. | N.D. | N.D. | 0.14 | N.D. |
| dl-XVIb | >40 | N.D. | 0.12 | 16 | 0.02 | N.D. | 0.018 | N.D. |
| Pentazocine | 4.9 | 36 | 12.0 | 187 | 10.1 | 90 | 12.2 | 82.2 |
| Nalorphine | 0.77 | 15 | 1.14 | >64 | 0.58 | 5.4 | 0.38 | 22.1 |
| Levallorphan | 26.3 (poor dose response) | N.D. | 0.29 | 46 | 0.32 | 5.4 | 0.086 | 12.6 |
| Cyclazocine | 0.047 | 4.0 | 0.81 | 24 | 0.12 | 2.7 | 0.040 | 3.7 |
| Naloxone | 40 | N.D. | 0.17 | 13.1 | 0.02 | 0.95 | 0.010 | 2.7 |
| l-XVIe | 44 | N.D. | 0.074 | N.D. | 0.013 | N.D. | 0.008 | N.D. |
| l-XVIb | 44 | N.D. | 0.07 | N.D. | 0.005 | N.D. | 0.006 | N.D. |
| l-XVIr | 0.18 | N.D. | 1.17 | N.D. | N.D. | N.D. | 0.10 | N.D. |

[1] A 50 percent reduction in number of phenylquinone induced writhings (Siegmund, E. A. et al., Proc. Soc. Biol. & Med. 95, 729; 1957).
[2] Antagonism of Straub Tail induced by oxymorphone (2 mg./kg. sc.) in 50 percent of mice.
[3] Antagonism of righting reflex loss induced by oxymorphone (1.5 mg./kg. sc.) in 50 percent of rats.
[4] A 50 percent reduction of analgesic effect induced by morphine (15 mg./kg. sc.) as measured by the rat tail flick procedure (Harris, L. S. and Pierson, A. K., J. Pharmacol. & Expt. Therap., 143, 141; 1964).
[5] N.D. - Not done.
[6] All values are reported in terms of the free base even though administered as an acid addition salt.

10. The compound of formula XXXX wherein $R^1$ is

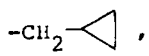

$R^2$ is H, $R^3$ is methyl, $R^4$ is tartrate salt thereof.

All of the compounds of the preferred embodiments herein are novel and valuable for their properties as analgesic and/or narcotic antagonist agents, or as intermediates in the preparation of compounds having these biological activities.

In particular, the compounds having the formula XVI are those which possess the most desirable properties; i.e., analgesic and/or narcotic antagonist properties. Some of these compounds also possess antitussive activity, a property generally inherent with analgetic activity.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

In vivo testing was conducted on the compounds designated herein as dl-XVIc, l-XVIc tartrate, d-XVIc tartrate, dl-XVIe, dl-XVId and dl-XVIb to determine It is apparent from the testing that compounds dl-XVIe, dl-XVId and dl-XVIb have weak subcutaneous analgesic activity but are relatively potent parenteral antagonists. At the same time, compounds dl-XVIc, and especially the resolved l-XVIc isomer, exhibits potent agonist and antagonist activity upon parenteral administration. The normal parenteral dosage range of the compounds of the present invention in adult humans is about 0.25 to 10 mg. three to four times a day. Orally the dose is in the range of about 2 to 50 mg. three or four times a day.

It has been reported in the literature that the compound haloperidol, 4[4-(p-chlorophenyl)-4-hydroxypiperidino]-4'-fluorobutyrophenone (Merck Index, 8th Edition, p. 515) has found some experimental use in the alleviation of narcotic addiction withdrawal symptoms. It is, therefore, a preferred embodiment of the present invention to combine haloperidol with the narcotic antagonists of the instant invention, particularly compounds dl-XVIe, dl-XVId and dl-XVIb, to produce a product not only preventing narcotic abuse, but at the same time providing supportive therapy in the absence of opiates.

Haloperidol is commonly administered orally in 0.5 to 5.0 mg. two or three times daily depending upon the severity of the illness. A dose of haloperidol in this range would be administered contemporaneously with an effective dose of the narcotic antagonist to produce the desired result.

Other combinations would include the narcotic antagonists in combination with anti-anxiety agents such as chlorodiazepoxide and diazepam, or phenothiazines like chlorpromazine, promazine or methotrimeptrazine.

EXAMPLES

Example 1

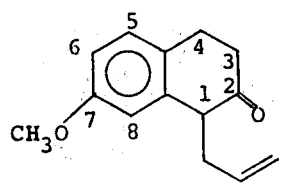

3,4-Dihydro-7-methoxy-1-allyl-2(1H)naphthalenone (II)a

To a stirred solution of 50 g. (0.284 mole) of Ia (3,4-dihydro-7-methoxy-2(1H)naphthalenone) dissolved in 200 ml. of dry benzene was added during 5–10 minutes and under nitrogen, 40.5 g. (0.5 mole) of pyrrolidine dissolved in 50 ml. of benzene. The mixture was refluxed for 1 hour and 5 ml. of water was collected in a Dean-Stark apparatus. The mixture was cooled and added slowly to 60.5 g. (0.5 mole) of allyl bromide dissolved in 300 ml. of benzene. The resulting mixture was refluxed for 3 hours. Then 200 ml. of water was added to the reaction and refluxing was resumed. After 30 minutes, the mixture was cooled, the benzene layer was separated, washed with water, followed by water saturated with sodium chloride, dried over sodium sulfate and evaporated to dryness. The residue was distilled to give 52.20 g. (85% yield) of IIa; b.p. 106°–112°/0.01–0.05 mm. The infrared (IR) and Nuclear Magnetic Resonance (NMR) spectra were consistent with the structure.

Anal. calc'd. for $C_{14}H_{16}O_2$: C, 77.74; H, 7.45. Found: C, 77.47; H, 7.50.

Example 2

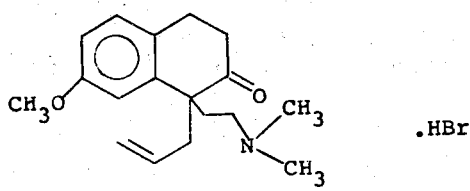

3,4-Dihydro-7-methoxy-1-allyl-1-(2-dimethylaminoethyl)-2(1H)naphthalenone hydrobromide (IIIa)

A mixture of 400 ml. dry benzene, 22g. (0.25 mole) of tert.-amyl alcohol and 10.62 g. (0.25 mole) of sodium hydride was refluxed under $N_2$ for 30 minutes or until all the hydride was consumed. Then 47.2 g. (0.22 mole) of IIa in 100 ml. of benzene was added slowly while distilling off the excess of amyl alcohol. Another 100 ml. of benzene was added and distilled off. Then 28 g. (0.3 mole) of 2-chloro-N,N-dimethylaminoethane in 100 ml. of benzene was added dropwise. The reaction mixture was refluxed for 20 hours, washed twice with water, and diluted with ether and extracted with 1N HCl. The acidic extract was warmed to 60° C. for 1 hour, cooled and extracted with ether to recover 15 g. of IIa. The acid extract was then cooled, basified with $NH_4OH$ and extracted with ether. It was dried over potasssium carbonate, treated with charcoal and after filtration, with dry HBr. There was obtained 33.87 g. (61.5%) of HBR salt of IIIa. After recrystallization from methanol/ether, it melted at 139°–140°. The IR and NMR were consistent with the structure.

Anal. calc'd. for $C_{18}H_{25}NO_2 \cdot HBr$: C, 58.69; H, 7.11; N, 3.80. Found: C, 58.63; H, 7.16; N, 3.59.

Example 3

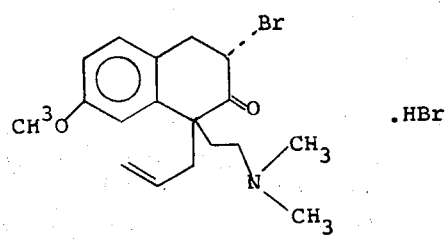

3-Bromo-3,4-dihydro-7-methoxy-1-allyl-1-(2-dimethylaminoethyl-2(1H)naphthalenone hydrobromide (IVa)

To a stirred solution of 15 g. (41 mmole) of IIIa in 100 ml. of methylene chloride and 300 ml. tetrahydrofuran (THF) in the dark, a solution of 20.58 g. (41.5 mmole) pyrrolidone hydrotribromide in 300 ml. of THF was added over a 4 hour period. After the addition, the reaction mixture was left overnight at room temperature. The solvents were evaporated to dryness and the solid residue recrystallized from 700 ml. of isopropanol to give 12.7 g. (68.5%) of IVa; m.p. 149°–150° C. The IR and NMR were consistent with the structure.

Anal. calc'd. for $C_{18}H_{24}NO_2Br \cdot HBr$: C, 48.34; H, 5.63; N, 3.13. Found: C, 48.64; H, 5.70; N, 3.14.

Example 4

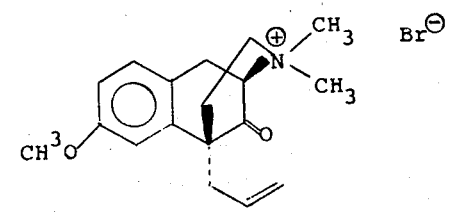

2′-Methoxy-2-methyl-5-allyl-9-oxo-6,7-benzomorphan methobromide (Va)

The HBr salt IVa (12.6 g., 0.028 mole) was dissolved in ice cold water, placed in a separatory funnel and covered with ether. Enough concentrated ammonium hydroxide was added to alkalanize the mixture and the free base of IV was extracted and separated as rapidly as possible. The ether was evaporated, and the residue was dissolved in acetone and left overnight. There was obtained 6.55 g. (65.5% yield) of solid Va. After recrystallization from isopropanol, it melted at 175°–177° C. The IR and NMR were consistent with the structure.

Anal. calc'd. for $C_{17}H_{21}NO_2 \cdot CH_3Br \cdot 1/2H_2O$: C, 57.60; H, 6.71; N, 3.73. Found: C, 57.44; H, 6.78; N, 3.58.

Example 5

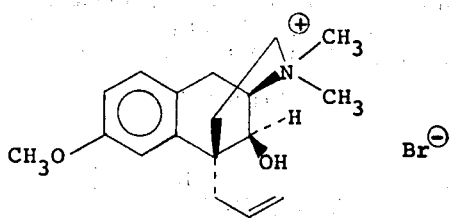

2'-Methoxy-2-methyl-5-allyl-9β-hydroxy-6,7-benzomorphan methobromide (VIa)

To a stirred suspension of Va [5.9 g., 0.0161 mole] in 50 ml. of anhydrous ethanol, was added 0.350 g. (0.009 mole) of $NaBH_4$. One hour after the addition, 0.800 g. of 48% HBr diluted with 10 ml. of water was added in small portions, and the reaction mixture was evaporated to dryness. The residue was taken up into methylene chloride, the inorganic material was filtered off and the solution was dried over sodium sulfate and evaporated to dryness. The solid residue was dissolved in a minimum of isopropanol and enough ether was added to crystalize VIa. There was obtained 4.2 g. of VIa (72.3% yield); m.p. 193° C. The IR and MNR spectra were consistent with the structure.

Anal. calc'd. for $C_{17}H_{23}NO_2 \cdot CH_3Br$: C, 58.69; H, 7.11; N, 3.80. Found: C, 58.89; H, 7.26; N, 3.71

Example 6

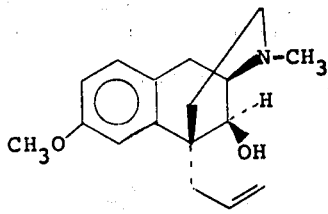

2'-Methoxy-2-methyl-5-allyl-9β-hydroxy-6,7-benzomorphan (VIIa)

To 50 ml. of boiling 1-octanol was added 4.87 g. (13.2 mmole) of VIa and the mixture was refluxed for 15 minutes. After cooling, the solution was diluted with ether and extracted with 2N HCl followed by two portions of 20 ml. of $H_2O$. The aqueous extracts were washed with petroleum ether (essentially n-hexane) to eliminate the traces of octanol, basified with ammonium hydroxide and extracted with ether, dried over sodium carbonate and evaporated. The oily residue crystallized upon addition of cyclohexane. Recrystallization from cyclohexane afforded 2.2 g. of VIIa in a yield of 61% m.p. 93°–94° C. The IR and NMR spectra are consistent with the structure.

Anal. calc'd. for $C_{17}H_{23}NO_2$: C, 74.69; H, 8.48; N, 5.12 Found: C, 74.64; H, 8.49; N, 5.12.

Example 7

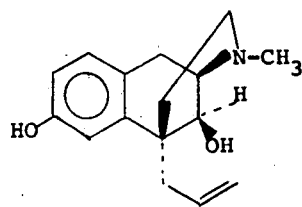

2'-Hydroxy-2-methyl-5-allyl-9β-hydroxy-6,7-benzomorphan (VIIIa).

A solution of 1 g. of VIIa (0.037 mole) in 20 ml. of dry methylene chloride was added slowly to a cooled (−10° C.) solution of 0.927 g. (0.037 mole) of $BBr_3$ in 20 ml. of methylene chloride. Upon completion of the addition, the ice bath was removed and the reaction mixture was left at room temperature overnight. The content of the flask was poured on crushed ice and concentrated ammonium hydroxide, followed by extraction with chloroform. After drying over sodium sulfate, there was obtained 0.46 g. of VIIIa as a solid; yield: 48%. It was recrystallized from toluene-petroleum ether; m.p. 60°–64° C. The IR and NMR spectra are consistent with the structure.

Anal. calc'd. for $C_{16}H_{21}NO_2$: C, 74.09; H, 8.16; N, 5.40. Found: C, 74.73; H, 8.25; N, 5.30.

Example 8

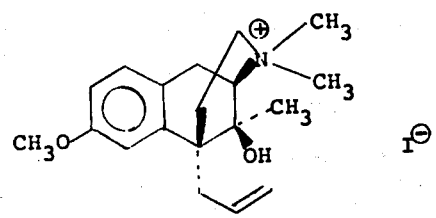

2'-Methoxy-2,9α-dimethyl-5-allyl-9β-hydroxy-6,7-benzomorphan methiodide (VIb)

To 5 g. (13.6 mmole) of Va was added rapidly a solution of Grignard reagent prepared from 11.35 g. (79 mmole) methyl iodide and 2.07 g. (85.0 mole) magnesium in 50 ml. of ether. After the addition, the reaction was stirred at room temperature until all the solid has dissolved (approximately 2 hours), then water (5 ml.) was added to the solution while cooling, followed by 15 ml. of 5N HCl and 5 g. of potassium iodide dissolved in 10 ml. of water. After stirring for 2 additional hours, the solid was filtered off. The product was recrystallized from water to give 4.3 g. (78% yield) of VIb; m.p. 184°–185° C. The IR and NMR were consistent with the structure.

Anal. calc'd. for $C_{18}H_{25}NO_2 \cdot CH_3I \cdot 1/2H_2O$: C, 52.06; H, 6.66; N, 3.19. Found: C, 52.31; H, 6.56; N, 3.19.

Example 9

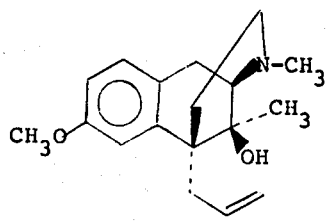

2'-Methoxy-2,9α-dimethyl-5-allyl-9β-hydroxy-6,7-benzomorphan (VIIb)

To 75 ml. of boiling 1-octanol was added 9.00 g. of VIb (0.021 mole) and the mixture refluxed for 15 minutes. After workup, as described in example 6, there was obtained 4.62 g. of VIIb as an oil which crystallized upon standing; m.p. 57° C. (Yield 75.5%). An oxalate salt was prepared and recrystallized from a mixture of methanol and ethyl ether; m.p. 180° C. (change 165°–175°). The IR and NMR spectra were consistent with the structure.

Anal. calc'd. for $C_{18}H_{25}NO_2.C_2H_2O_4 1/2CH_3OH$: C, 62.49; H, 7.54; N, 3.55. Found: C, 62.55; H, 7.19; N, 3.81.

Example 10

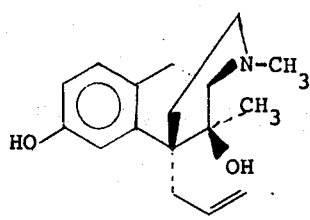

2'-Hydroxy-2,9α-dimethyl-5-allyl-9β-hydroxy-6,7-benzomorphan (VIIIb)

To a stirred and ice-salt cooled solution of 0.450 g. (1.7 mmole) $BBr_3$ in 10 ml. of methylene chloride was added slowly 0.500 g. (1.7 mmole) of VIIa dissolved in 10 ml. of dry methylene chloride. After working up the product as in example 7, there was obtained 0.47 g. of crude VIIIb. The crude material was dissolved in acetone and precipitated by oxalic acid. There was obtained 0.300 g. of the oxalate salt of VIIIb (47.5% yield). It was recrystallized from acetone; m.p. 195° (dec.). The IR and NMR spectra were consistent with the structure.

Anal. Calc'd. for $C_{17}H_{23}NO_2.C_2H_2O_4$: C, 62.79; H, 6.93; N, 3.85. Found: C, 63.00; H, 7.01; N, 4.04.

Example 11

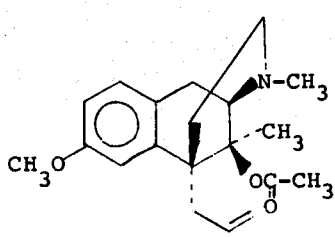

2'-Methoxy-2,9α-dimethyl-5-allyl-9β-hydroxy-6,7-benzomorphan acetate (IXb)

To 1 ml. of acetic anhydride was added 0.287 g. of VIIb (0.001 mole) and 0.080 g. of pyridine. The resulting solution was refluxed for one hour and the solvents evaporated. The residue was taken up in ether and washed with a dilute solution of ammonium hydroxide. The ether layer was dried over sodium sulfate and evaporated to dryness to give a theoretical amount (0.320 g.) of crude IXb as an oil. An oxalate salt of IXb was prepared in acetone and recrystallized from a mixture of methanol and acetone: m.p. 181°–182° C. The IR and NMR were consistent with the structure.

Anal. calc'd. for $C_{20}H_{27}NO_3.C_2H_2O_4$: C, 62.99; H, 6.96; N, 3.33. Found: C, 62.77; H, 7.15; N, 3.36.

Example 12

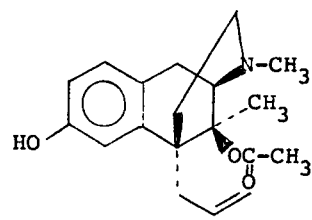

2',9β-Dihydroxy-2,9α-dimethyl-5-allyl-6,7-benzomorphan-9β-acetate (Xb)

A 5 ml. solution of methylene chloride containing 0.320 g. of IXb (0.001 mole) was added with stirring to a cooled solution (−10° C.) of $BBr_3$ [0.511 g., 0.002 mole]. The ice bath was then removed and the reaction mixture was left at room temperature for 30 minutes. It was poured into a mixture of crushed ice and concentrated ammonium hydroxide and extracted with chloroform. After drying over sodium sulfate and evaporation of the solvent, a residue of 0.275 g. of crude Xb was obtained. It was recrystallized from methanol to give 0.250 g. of Xb; yield; 87%; m.p. 193°–194° C. The IR and NMR were consistent with the strucuture.

Anal. calc'd. for $C_{19}H_{25}NO_3$: C. 72.35; H, 7.98; N, 4.44. Found: C, 72.20; H, 8.05; N, 4.34.

Example 13

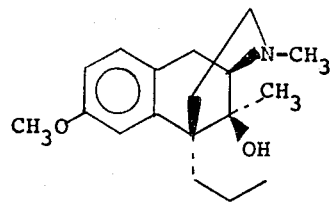

2'-Methoxy-2,9α-dimethyl-5-propyl-9β-hydroxy-6,7-benzomorphan (VIIc)

A solution of 1 g. (3.5 mmole) of VIIb in 20 ml. of absolute ethanol was placed into an hydrogenation bottle containing 0.110 g. of 10% palladium on charcoal. After shaking 2 hours at room temperature and 60 psi of $H_2$, the catalyst was filtered off and the solvent evaporated. There was obtained 1.0 g. of an oil which crystallized upon standing. It was recrystallized from petroleum ether (30°–60°) to give a 95% yield of VIIc; m.p. 101°–102° C. The IR and NMR spectra were consistent with the product.

Example 14

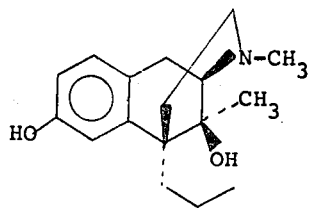

2'-9β-Dihydroxy-2,9α-dimethyl-5-propyl-6,7-benzomorphan (VIIIc)

A solution of 0.500 g. (.0019 mole) of VIIc in 2 ml. of $CH_2Cl_2$ was added slowly to a solution of 1.3 g. (0.005 mole) of $BBr_3$ in 5 ml. of methylene chloride maintained at −10° C. After the addition, the ice-salt bath was removed and the mixture was left at room temperature for 30 minutes. It was then poured into crushed ice and concentrated ammonium hydroxide and extracted with chloroform. The chloroform extract was acidified with 1N HCl, the acidic extract washed with chloroform and basified before re-extraction with chloroform. After drying over sodium sulfate, there was obtained 0.370 g. of VIIIc as an oil which crystallized readily out of benzene. The yield of VIIIc was 78%; m.p. 165°–166° C. The IR and NMR spectra were consistent with the structure.

Anal. calc'd. for $C_{17}H_{25}NO_2$: C, 74.14; H, 9.15; N, 5.08. Found: C, 74.02; H, 9.08; N, 5.13

Example 15

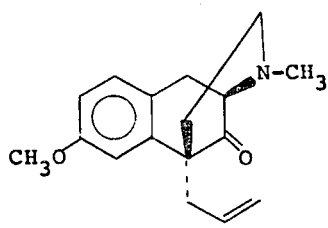

2'-Methoxy-2-methyl-5-allyl-9-oxo-6,7-benzomorphan (XIa)

The suspension of 2 g. (5.46 mmole) Va in 25 ml. 1-octanol was heated under reflux and nitrogen atmosphere for 15 minutes. After cooling, the mixture was poured into 40 ml. of 0.5N HCl and extracted twice with 100 ml. of petroleum ether to remove octanol. The water layer was basified with aqueous ammonia and the free base extracted with benzene to yield, after drying and evaporation of solvent, 1.23 g. of an oil (XIa). The oil was stirred with a solution of 350 mg. oxalic acid in 5 ml. water for 1 hour, and it was left at 5° for 16 hours. Separated solid was filtered off to yield 980 mg. (47%) of XIa oxalate, containing one mole of water of crystallization; m.p. 156°–162° C. The product recrystallized from water melted at 160°–161° C. with loss of water at 110° C.

Anal. calc'd. for $C_{17}H_{21}NO_2 \cdot C_2H_2O_4 \cdot H_2O$: C, 60.15; H, 6.64; N, 3.69. Found: C, 60.52; H, 6.72; N, 3.70.

Example 16

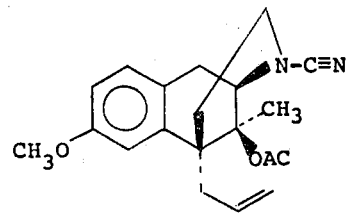

2'-Methoxy-2-cyano-5-allyl-9α-methyl-9β-hydroxy-6,7-benzomorphan acetate (XIIb)

A 50 ml. benzene solution of 5.6 g. (0.017 mole) of IXb is added slowly with stirring to 2 g. (0.019 mole) of cyanogen bromide in 20 ml. of benzene and refluxed overnight. After cooling the reaction mixture is washed with water, dried over sodium sulfate and evaporated to dryness. The residue is taken in boiling ethanol and upon cooling 4.92 g. of pure XIIb crystallizes for a yield of 85%; m.p. 124°–125° C. The IR and NMR spectra are consistent with the structure.

Anal. calc'd. for $C_{20}H_{24}N_2O_3$: C, 70.56; H, 7.10; N, 8.22. Found: C, 70.30; H, 7.20; N, 8.28.

Example 17

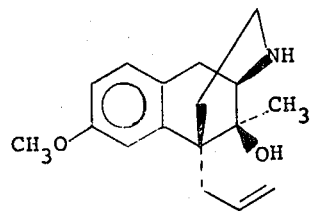

2'-Methoxy-5-allyl-9α-methyl-9β-hydroxy-6,7-benzomorphan (XIIIb)

A solution of 1 g. (.003 mole) of XIIb in 5 ml. of THF was added to a slurry of 0.250 g. of lithium aluminum hydride (LAH) in 10 ml. of THF. The resulting mixture was refluxed for three hours. After working up the usual way with 0.250 g. of $H_2O$, 0.187 g. of 20% NaOH and 0.875 of water, there was obtained 0.830 g. of crude XIIIb as an oil which upon addition of cyclohexane crystallized readily. It was recrystallized from the same solvent to give 0.615 g. of pure XIIIb; m.p. 80°–82° C.; in a yield of 75%. The IR and NMR spectra were consistent with the structure.

Anal. calc'd. for $C_{17}H_{23}NO_2$: C, 74.69; H, 8.48; N, 5.12. Found: C, 74.39; H, 8.64; N, 5.02.

Example 18

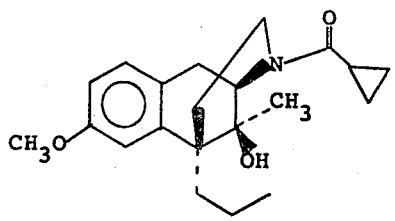

2'-Methoxy-2-cyclopropylcarbonyl-5-allyl-9α-methyl-9β-hydroxy-6,7-benzomorphan (XIVb)

To a solution of 0.300 g. (0.0011 mole) of XIIIb and 0.050 g. of triethylamine (TEA) in 5 ml. of methylene chloride was added slowly with cooling a solution of 0.110 g. (.00107 mole) of cyclopropane carboxylic acid chloride in 5 ml. of methylene chloride, and left at room temperature for 30 minutes. The reaction mixture was then washed with water and diluted with ether. The organic phase was dried over potassium carbonate and evaported to dryness. The oily residue was triturated with petroleum ether and crystallized at once to give 0.330 g. of XIVb (yield 97%). After recrystallization from ligroin or petroleum ether, it melts at 121°–122° C. The IR and NMR spectra were consistent with the structure.

Anal. calc'd. for $C_{21}H_{27}NO_3$: C, 73.86; H, 7.97; N, 4.10. Found: C, 74.22; H, 8.03; N, 4.09

Example 19

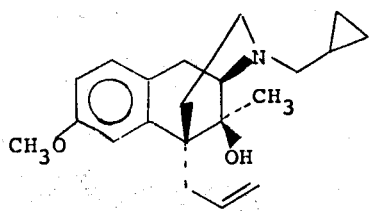

2'Methoxy-2-cyclopropylmethyl-5-allyl-9α-methyl-9β-hydroxy-6,7-benzomorphan (XVb)

A solution of 1.2 g. (2.9 mmole) of XIVb in 10 ml. of THF was added slowly to a slurry of 0.250 g. of LAH in 10 ml. of THF. The resulting mixture was refluxed overnight and after usual workup we obtained 0.930 g. of XVb as a colorless oil (theoretical yield). The HCl salt was precipitated out of ether using dry HCl, and it was recrystallized from a mixture of methanol and ether; m.p. 176°–177° C. The IR and NMR spectra were consistent with the structure.

Anal. calc'd. for $C_{21}H_{29}NO_2.HCl$: C, 69.30; H, 8.30; N, 3.84. Found C, 68.77; H, 8.41; N, 3.67.

Example 20

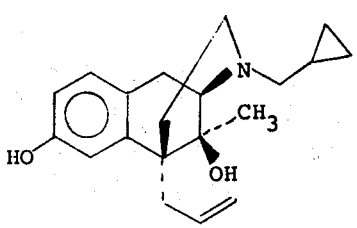

2',9β-Dihydroxy-2-cyclopropylmethyl-5-allyl-9α-methyl-6,7-benzomorphan (XVIb)

To 0.320 g. (1.27 mmole) of $BBr_3$ in 10 ml. of methylene chloride maintained at −10° C., was added slowly 0.420 g. (1.27 mmole) of XVb dissolved in 10 ml. of methylene chloride. After the addition, the reaction mixture was stirred overnight at room temperature. The reaction mixture was poured on crushed ice and concentrated ammonium hydroxide, extracted with chloroform and dried over sodium sulfate. After evaporation of the solvent, there was obtained 0.450 g. of a residue showing three spots on thin layer chromatography (TLC). That mixture was chromatographed over 30 g. of aluminum oxide using chloroform as the eluent. Thus there was obtained 0.210 g. of pure XVIb for a 50% yield. It was recrystallized from a mixture of benzene and petroleum ether; m.p. 122°–123° C. The IR and NMR spectra were consistent with the structure.

Anal. calc'd. for $C_{20}H_{27}NO_2$: C, 76.63; H, 8.68; N, 4.46. Found: C, 76.62; H, 8.61; N, 4.36.

Example 21

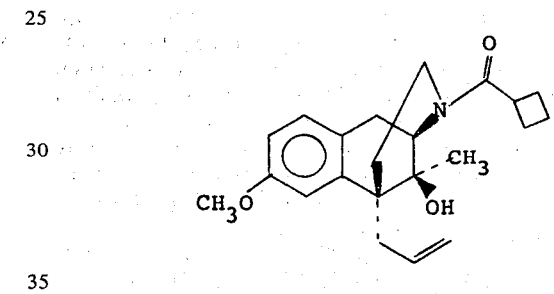

2'-Methoxy-2-cyclobutylcarbonyl-5-allyl-9α-methyl-9β-hydroxy-6,7-benzomorphan (XIVc)

Compound XIVc was prepared in the same manner as described for its analogue XIVb in example 18 and obtained in a yield of 82%. It was recrystallized from ligroin (essentially n-hexane) to give a melting point of 131°–132° C. The IR and NMR spectra were consistent with the structure.

Anal. calc'd. for $C_{22}H_{29}NO_2$: C, 74.33; H, 8.22; N, 3.94. Found: C, 74.67; H, 8.40; N, 4.07.

Example 22

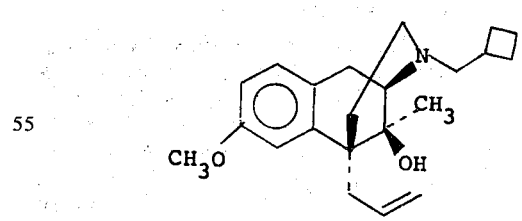

2'-Methoxy-2-cyclobutylmethyl-5-allyl-9α-methyl-9β-hydroxy-6,7-benzomorphan (XVc)

Compound XVc was prepared in the same manner as described for compound XVc in example 19 and also obtained as a colorless oil in good yield. The HCl salt was precipitated out of ether with dry HCl and recrystallized from a mixture of methanol and ether; m.p.

211°–212° C. The IR and NMR spectra were consistent with the structure.

Anal. calc'd. for $C_{22}H_{31}NO_2 \cdot HCl \cdot 1/2\ H_2O$: C, 68.28; H, 8.50; N, 3.61. Found: C, 68.08; H, 8.12; N, 3.61.

Example 23

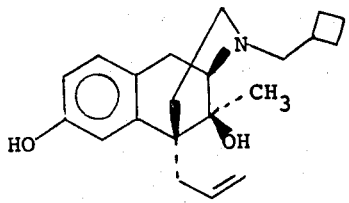

2',9β-Dihydroxy-2-cyclobutylmethyl-5-allyl-9α-methyl-6,7-benzomorphan (XVIc)

To a stirred and ice-salt cooled solution of 0.452 g. (1.8 mmole) of $BBr_3$ in 5 ml. of methylene chloride was slowly added 0.610 g. (.0018 mole) of XVc in 5 ml. of methylene chloride. The resulting mixture was left at room temperature overnight. After the usual workup, we obtained a residue of 0.600 g. showing three spots on TLC. Separation was achieved on 60 g. aluminum oxide using chloroform as the eluent. Thus we obtained 0.290 g. of XVIc as a semi-solid; yield (49.5%).

The HCl salt of XVIc was prepared by the usual way and it was recrystallized out of methanol and ether; m.p. 243°–244° C. dec. The IR and NMR spectra were consistent with the structure.

Anal. calc'd. for $C_{21}H_{29}NO_2 \cdot HCl$: C, 69.49; H, 8.05; N, 3.85. Found: C, 69.80; H, 8.39; N, 3.74.

Example 24

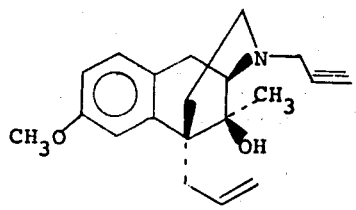

2'-Methoxy-2-propargyl-5-allyl-9β-hydroxy-9α-methyl-6,7-benzomorphan (XVd).

A mixture of 0.500 g. (1.8 mmole) of XIIIb, 0.300 g. of sodium bicarbonate and 0.225 g. (1.8 mmole) of propargyl bromide in 5 ml. of dry dimethylformamide (DMF) was stirred overnight at room temperature. The reaction mixture was then diluted with ether and filtered. The filtrate was extracted with 0.05N HCl, the layers separated and the acidic layer made alkaline with concentrated ammonium hydroxide before extraction with ether. After drying over potassium carbonate, there was obtained 0.510 g. of a colorless oil which crystallized at once; m.p. 95°–96°C. of XVd; yield 91%. The HCl salt was prepared in the usual way and recrystallized in a mixture of methanol-ether; m.p. 210°–212°C. The IR and NMR spectra were consistent with the structure.

Anal. calc'd. for $C_{20}H_{25}NO_2 \cdot HCl$: C, 69.05; H, 7.53; N, 4.02. Found: C, 69.13; H, 7.62; N, 3.98.

Example 25

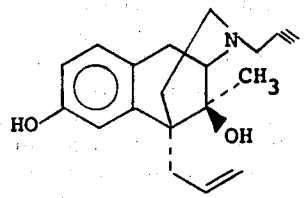

2',9β-Dihydroxy-2-propargyl-5-allyl-9α-methyl-6,7-benzomorphan (XVId)

A solution of 0.420 g. (1.35 mmole) of XVd in 10 ml. of methylene chloride was added slowly to a solution of 1.4 mmole (0.350 g.) of $BBr_3$ in 10 ml. of methylene chloride maintained at −10°C. The resulting mixture was stirred overnight at room temperature. After usual workup, there was obtained 0.360 g. of an oil. It was dissolved in methanol and upon cooling and addition of water, there was obtained 0.200 g. of crystalline XVId (yield 53%); m.p. 159°–161° C. The IR and NMR spectra were consistent with the structure.

Anal. calc'd for $C_{19}H_{23}NO_2$: C, 76.73; H, 7.79; N, 4.71. Found, C, 76.84; H, 7.89; N, 4.69.

Example 26

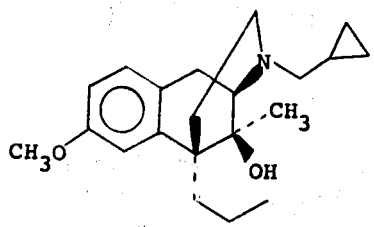

2'-Methoxy-2-cyclopropylmethyl-5-propyl-9β-hydroxy-9α-methyl-6,7-benzomorphan (XVe)

A solution of 0.600 g. (1.87 mmole) of XVb in 20 ml. of absolute ethanol was introduced into an hydrogenation bottle containing 0.100 g. of palladium 10% on charcoal. The resulting mixture was shaken under 60 psi of hydrogen for 2 hours at room temperature. The catalyst was filtered off and the filtrate evaporated to dryness. The residue (0.600 g.) was crystallized from absolute ethanol; m.p. 90°–91° C. The yield is 95+% of XVe. The IR and NMR spectra were consistent with the structure.

Example 27

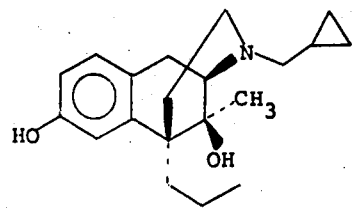

2',9β-Dihydroxy-2-cyclopropylmethyl-5-propyl-9α-methyl-6,7benzomorphan (XVIe)

A solution of 0.340 g. (1.03 mmole) of XVe in 15 ml. of dry methylene chloride was added slowly to a stirred solution of 0.750 g. (3 mmole) of $BBr_3$ kept at $-10°$ C. After the addition, the ice-salt bath was removed and the reaction mixture was allowed to warm up to room temperature. After the usual workup, there was obtained an oil which when dissolved in hot methanol crystallized upon cooling; m.p. 144°–145° C. (68%).

Anal. calc'd. for $C_{20}H_{29}NO_2$: C, 76.14; H, 9.26; N, 4.44. Found: C, 76.37; H, 9.41; N, 4.24.

Example 28

Preparation of 3,4-Dihydro-7-methoxy-1-methyl-2[H]naphthalenone (IIf)

Substitution in the procedure of example 1 for the allyl bromide used therein of an equimolar quantity of methyl iodide produced the title product IIf.

Example 29

Preparation of 3,4-Dihydro-7-methoxy-1-methyl-1-(2-dimethylaminoethyl)-2[1H]naphthalenone hydrobromide (IIIf)

Substitution in the procedure of example 2 for the compound II using therein of an equimolar quantity of compound IIIf obtained in example 28 produced the title product IIIf.

Example 30

Preparation of 3-Bromo-3,4-dihydro-7-methoxy-1-methyl-1-(2-dimethylaminoethyl)-2[1H]naphthalenone hydrobromide (IVf)

Substitution in the procedure of example 3 for the compound III used therein of an equimolar quantity of compound IIIf obtained in example 29 produced the title produce IVf.

Example 31

Preparation of 2'-Methoxy-2,5-dimethyl-9-oxo-6,7benzomorphan methobromide (Vf)

Substitution in the procedure of example 4 for the compound IV used therein of an equimolar quantity of IVf obtained in example 30 produced the title compound Vf.

Example 32

Preparation of 2'-Methoxy-2,5,9α-trimethyl-9β-hydroxy-6,7-benzomorphan methiodide (VIf)

Substitution in the procedure of example 8 for the compound Va used therein of an equimolar quantity of compound Vf obtained in example 31 produced the title product VIf.

Example 33

Preparation of 2'-Methoxy-2,5,9α-trimethyl-9β-hydroxy-6,7-benzomorphan (VIIf)

Substitution in the procedure of example 9 for the compound VIb used therein of an equimolar quantity of compound VIf obtained in example 32 produced the title compound VIIf; m.p. 139.0°–143.0° (as the hydrate).

Example 34

Preparation of 2'-Methoxy-2,5,9α-trimethyl-9β-hydroxy-6,7-benzomorphan acetate (IXf)

Substitution in the procedure of example 11 for the compound VIIb used therein of an equimolar quantity of compound VIIf obtained in example 33 produced the title compound IXf.

Example 35

Preparation of 2'-Methoxy-2-cyano-5,9α-dimethyl-9β-hydroxy-6,7-benzomorphan acetate (XIIf)

Substitution in the procedure of example 16 for the compound IXb used therein of an equimolar quantity of compound IXf obtained in example 34 produced the title compound XIIf.

Example 36

Preparation of 2'-Methoxy-5,9α-dimethyl-9β-hydroxy-6,7-benzomorphan (XIIIf)

Substitution in the procedure of example 17 for the compound XIIb used therein of an equimolar quantity of compound XIIf produced the title compound XIIIf; m.p. 147.0°–148.0° C. The IR and NMR spectra were consistent with the structure.

Anal. calc'd. for $C_{15}H_{21}NO_2$: C, 72.84; H, 8.56; N, 5.66. Found: C, 73.12; H, 8.63; N, 5.82.

Example 37

Preparation of 2'-Methoxy-2-cyclopropylmethyl-5,9α-dimethyl-9β-hydroxy-6,7-benzomorphan (XVf)

A solution of compound XIIf (0.005 moles) in 25 ml. methylene chloride and 7.5 ml. triethylamine was treated with cyclopropylcarbonyl chloride (3 ml.) with stirring. This mixture was stirred for 18 hours and then treated with dilute sodium carbonate. The layers were separated and the aqueous layer extracted with methylene chloride. Drying and concentration of the methylene chloride extracts gave 2'-methoxy-2-cyclopropylcarbonyl-5,9-dimethyl-9β-hydroxy-6,7-benzomorphan as an oil (XIVf). This material was taken up in tetrahydrofuran (30 ml.) and added to a stirred suspension of lithium aluminum hydride (1.0 g.) in tetrahydrofuran (20 ml.). After an 18 hour reflux period, this mixture was cautiously treated with 3 ml. saturated sodium sulfate and warmed until solids were white. Removal of the solids by filtration and concentration of the filtrates gave an oil (XVf) which was converted to its hydrobromide salt, m.p. 242°–244°C.

Anal. calc'd. for $C_{19}H_{27}NO_2 \cdot HBr$: C, 59.68; H, 7.38; N, 3.66. Found: C, 59.31; H, 7.52; N, 3.35

Example 38

Preparation of 2',9β-dihydroxy-2-cyclopropylmethyl-5,9α-dimethyl-6,7-benzomorphan (XVIf)

Substitution in the procedure of Example 20 for the compound XVb used therein of an equimolar quantity of compound XVf produces the title compound XVIf.

Example 39

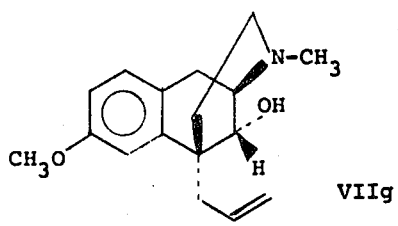

Preparation of 5-Allyl-9α-hydroxy-2'-methoxy-2-methyl-6,7-benzomorphan (VIIg)

A solution of diisobutylaluminum hydride (62 ml. of a 25% solution, 60 mmole) was diluted with 150 ml. of dry tetrahydrofuran and cooled at −40° to −50° under $N_2$. Then a solution of 8.58 g. of compound XIa (31.6 mmole) in 100 ml. of dry tetrahydrofuran was slowly added from a dropping funnel. After 1 hour, 5 ml. of water was carefully added, and the gelatinous material evaporated. The residue was dissolved in ether, washed with water, dried over sodium sulfate and evaporated to dryness leaving 8.88 g. of oil. Crystallization from ether-petroleum ether (essentially n-hexane) and chromatography of the mother liquor on silica gel afforded 8.23 g. (95%) of title compound. Recrystallization from acetone-ether-petroleum ether gave an analytical sample; m.p. 73°–78°.

Anal. calc'd. for $C_{17}H_{23}NO_2$: C, 74.69; H, 8.48; N, 5.12. Found: C, 74.26; H, 8.73; N, 5.19.

Example 40

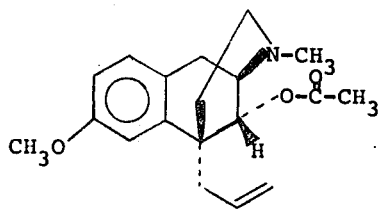

Preparation of 2'-Methoxy-2-methyl-5-allyl-9α-hydroxy-6,7-benzomorphan Acetate (IXg)

Substitution in the procedure of example 11 for the compound VIIb used therein of an equimolar amount of compound VIIg produces the title compound IXg.

Example 41

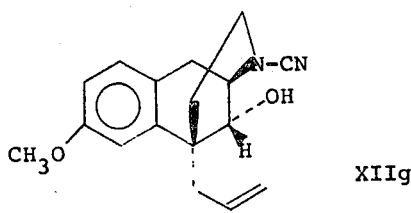

Preparation of 2'-Methoxy-2-cyano-5-allyl-9α-hydroxy-6,7-benzomorphan (XIIg)

Substitution in the procedure of example 16 for the compound IXb used therein of an equimolar quantity of IXg produces compound XIIg.

Example 42

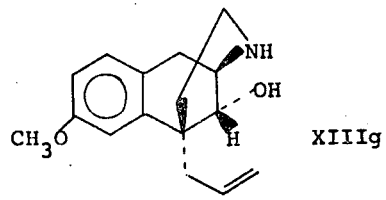

Preparation of 2'-Methoxy-5-allyl-9α-hydroxy-6,7-benzomorphan (XIIIg)

Substitution in the procedure of example 17 for the compound XIIb used therein of an equimolar quantity of XIIg produces compound XIIIg.

Example 43

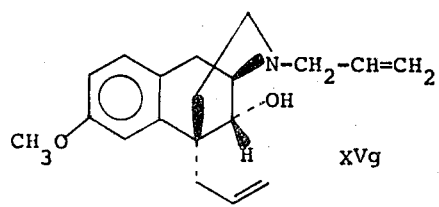

Preparation of 2'-Methoxy-2,5-diallyl-9α-hydroxy-6,7-benzomorphan (XVg)

Substitution in the procedure of example 24 for the propargyl bromide used therein of an equimolar quantity of allyl bromide produces the title compound XVg.

Example 44

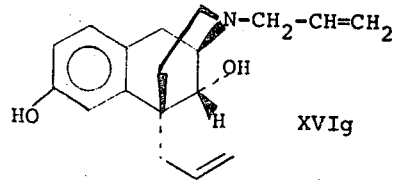

Preparation of 2',9α-Dihydroxy-2,5-diallyl-6,7-benzomorphan (XVIg)

Substitution in the procedure of example 25 for the compound XVd used therein of an equimolar quantity of compound XVg produces the title compound XVIg.

Example 45

Preparation of
5-Allyl-2'-methoxy-2,9β-dimethyl-9α-hydroxy-6,7-benzomorphan (VIIh)

A solution of methyllithium in ether (71 ml. of a 5% solution, 115 mmole) was transferred with a syringe to a two liters flask under $N_2$, evaporated to dryness and covered with 500 ml. of dry petroleum ether (essentially n-hexane). To the vigorously stirred suspension (under $N_2$) thus obtained, was added dropwise a solution of 14.60 g. (53.8 mmole) of compound XIa in 250 ml. of dry petroleum ether (30–65). The reaction mixture was then stirred at 20°–25° for 19 hours. A solution of methyllithium in ether (15 ml. of a 5% solution, 24 mmole) was added and the mixture stirred for 1.5 hour to complete the reaction. Water was slowly added to destroy the excess of methyllithium and the organic phase was washed with water.

The water phase was extracted with ether, dried over sodium sulfate, and evaporated to dryness leaving 14.51 g. (93%) of an oil which was a mixture of compound VIIb (40%) and the title compound (VIIh) as estimated by NMR.

The NMR spectrum showed two distinct signals for —$CH_3$—C—OH at $\delta = 1.0$ for compound VIIb and $\delta = 1.58$ for compound VIIh with tetramethylsilane as a reference standard. After treatment with charcoal, the free base (13.05 g.) mixture was dissolved in 90 ml. of 95% ethanol and added to a boiling solution of 11.96 g. of picric acid in 150 ml. of 95% ethanol.

The solution was kept at 5° for 60 hours and 21.88 g. of a yellow solid which was a mixture of VIIb and VIIh (20:80) was filtered. Two recrystallizations from dioxane and 95% ethanol afforded 15.3 g. (58%) of the α-isomer VIIh; m.p. 209°–212°C.

Treatment of the free base with oxalic acid in methanol and ether gave a solid which after recrystallization afforded an analytical sample, m.p. 208°–209° (VIIh oxalate).

Anal. calc'd. for $C_{18}H_{25}NO_2 \cdot C_2H_2O_4$: C, 73.78; H, 7.21; N, 3.71. Found: C, 73.78; H, 7.41; N, 3.92.

The mother liquor was concentrated at 6.16 g. (24%) of the β-isomer VIIb crystallized out. Recrystallization from acetone-ether gave a sample melting at 175°–178°. The free base of VIIb was found to be identical with a sample obtained from another source.

Example 46

Preparation of
5-Allyl-2'-methoxy-2,9β-dimethyl-9α-hydroxy-6,7-benzomorphan acetate (IXh)

Substitution in the procedure of example 11 for the compound VIIb used therein of an equimolar amount of compound VIIh produces the title compound IXh.

Example 47

Preparation of
2'-Methoxy-2-cyano-5-allyl-9β-methyl-9α-hydroxy-6,7-benzomorphan Acetate (XIIh)

Substitution in the procedure of example 16 for the compound IXb used therein of an equimolar quantity of IXh produces the title compound XIIh.

Example 48

Preparation of
2'-Methoxy-5-allyl-9β-methyl-9α-hydroxy-6,7-benzomorphan (XIIIh)

Substitution in the procedure of example 17 for the compound XIIb used therein of an equimolar amount of compound XIIh produces the title product XIIIh.

Example 49

Preparation of
2'-Methoxy-2-cyclopropylcarbonyl-5-allyl-9β-9α-hydroxy-6,7-benzomorphan (XIVh)

Substitution in the procedure of example 18 for the compound XIIIb used therein of an equimolar amount of XIIIh produces the title compound XIVh.

Example 50

Preparation of
2'-Methoxy-2-cyclopropylmethyl-5-allyl-9α-methyl-9β-hydroxy-6,7-benzomorphan (XVh)

Substitution in the procedure of example 19 for the compound XVb used therein of an equimolar quantity of compound XIVh produces the title compound XVh.

Example 51

Preparation of
2',9α-dihydroxy-2-cyclopropylmethyl-5-allyl-9β-methyl-6,7-benzomorphan (XVIh)

Substitution in the procedure of example 20 for the compound XVb used therein of an equimolar quantity of XVh produces the title compound XVIh.

Example 52

Preparation of
3,4-Dihydro-7-methoxy-1-ethyl-2-[1H]naphthalenone (IIj)

Substitution in the procedure of example 1 for the allyl bromide used therein of an equimolar quantity of ethyl bromide produces the title product IIj.

Example 53

Preparation of
3,4-Dihydro-7-methoxy-1-ethyl-1-(2-dimethylaminoethyl)-2[1H]naphthalenone hydrobromide (IIIj)

Substitution in the procedure of example 2 for the compound II used therein of an equimolar quantity of compound IIj obtained in example 52 produces the title product IIIj.

Example 54

Preparation of
3-Bromo-3,4-dihydro-7-methoxy-1-ethyl-1-(2-dimethylaminoethyl)-2[1H]naphthalenone hydrobromide (IVj)

Substitution in the procedure of example 3 for the compound III used therein of an equimolar quantity of compound IIIj obtained in example 53 produces the title product IVj.

Example 55

Preparation of
2'-Methoxy-2-methyl-5-ethyl-9-oxo-6,7-benzomorphan methobromide (Vj)

Substitution in the procedure of example 4 for the compound IV used therein of an equimolar quantity of IVj obtained in example 54 produces the title compound Vj.

Example 56

Preparation of
2'-Methoxy-2,9-dimethyl-5-ethyl-9β-hydroxy-6,7-benzomorphan methiodide (VIj)

Substitution in the procedure of example 8 for the compound Va used therein of an equimolar quantity of compound Vj obtained in example 55 produces the title product VIj.

Example 57

Preparation of
2'-Methoxy-2,9α-dimethyl-5-ethyl-9β-hydroxy-6,7-benzomorphan (VIIj)

Substitution in the procedure of example 9 for the compound VIb used therein of an equimolar quantity of compound VIj obtained in example 56 produces the title compound VIIj.

Example 58

Preparation of
2'-Methoxy-2,9α-dimethyl-5-ethyl-9β-hydroxy-6,7-benzomorphan Acetate (IXj)

Substitution in the procedure of example 11 for the compound VIIb used therein of an equimolar quantity of compound VIIj obtained in example 57 produces the title compound IXj.

Example 59

Preparation of
2'-Methoxy-2-cyano-9α-methyl-5-ethyl-9β-hydroxy-6,7-benzomorphan acetate (XIIj)

Substitution in the procedure of example 16 for the compound IXb used therein of an equimolar quantity of compound IXj obtained in example 58 produces the title compound XIIj.

Example 60

Preparation of
2'-Methoxy-9α-methyl-5-ethyl-9β-hydroxy-6,7-benzomorphan (XIIIj)

Substitution in the procedure of example 17 for the compound XIIb used therein of an equimolar quantity of compound XIIj produces the title compound XIIIj.

Example 61

Preparation of
2'-Methoxy-2-cyclopropylmethyl-9α-methyl-5-ethyl-9β-hydroxy-6,7-benzomorphan (XVj)

Substitution in the procedure of example 37 for the compound XIIIf used therein of an equimolar quantity of compound XIIIj produces the title compound XVj.

Example 62

Preparation of 2',
9β-Dihydroxy-2-cyclopropylmethyl-9α-methyl-5-ethyl-6,7-benzomorphan (XVIj)

Substitution in the procedure of example 20 for the compound XVb used therein of an equimolar quantity of compound XVj produces the title compound XVIj.

Example 63

Preparation of
3,4-Dihydro-7-methoxy-1-benzyl-2[H]naphthalenone (IIk)

Substitution in the procedure of example 1 for the allyl bromide used therein of an equimolar quantity of benzyl bromide produces the title product IIk.

Example 64

Preparation of
3,4-Dihydro-7-methoxy-1-benzyl-1-(2-dimethylaminoethyl)-2[1H]naphthalenone hydrobromide (IIIk)

Substitution in the procedure of example 2 for the compound II using therin of an equimolar quantity of compound IIk obtained in example 63 produces the title product IIIk.

Example 65

Preparation of
3-Bromo-3,4-dihydro-7-methoxy-1-benzyl-1-(2-dimethylaminoethyl)-2[1H]naphthalenone hydrobromide (IVk)

Substitution in the procedure of example 3 for the compound III used therein of an equimolar quantity of compound IIIk obtained in example 64 produces the title product IVk.

Example 66

Preparation of
2'-Methoxy-2-methyl-5-benzyl-9-oxo-6,7-benzomorphan methobromide (Vk)

Substitution in the procedure of example 4 for the compound IV used therein of an equimolar quantity of IVk obtained in example 65 produces the title compound Vk.

Example 67

Preparation of
2'-Methoxy-2,9α-dimethyl-5-benzyl-9β-hydroxy-6,7-benzomorphan methiodide (VIk)

Substitution in the procedure of example 8 for the compound Va used therein of an equimolar quantity of compound Vk obtained in example 66 produces the title product VIk.

Example 68

Preparation of
2'-Methoxy-2,9α-dimethyl-5-benzyl-9β-hydroxy-6,7-benzomorphan (VIIk)

Substitution in the procedure of example 9 for the compound VIb used therein of an equimolar quantity of compound VIk obtained in example 67 produces the title compound VIIk.

Example 69

Preparation of 2'-Methoxy-2,9α-dimethyl-5-benzyl-9β-hydroxy-6,7-benzomorphan acetate (IXk)

Substitution in the procedure of example 11 for the compound VIIb used therein of an equimolar quantity of compound VIIk obtained in example 68 produces the title compound IXk.

Example 70

Preparation of 2'-Methoxy-2-cyano-5-benzyl-9α-methyl-9β-hydroxy-6,7-benzomorphan acetate (XIIk)

Substitution in the procedure of example 16 for the compound IXb used therein of an equimolar quantity of compound IXk obtained in example 69 produces the title compound XIIk.

Example 71

Preparation of 2'-Methoxy-9α-methyl-5-benzyl-9β-hydroxy-6,7-benzomorphan (XIIIk)

Substitution in the procedure of example 17 for the compound XIIb used therein of an equimolar quantity of compound XIIk produces the title compound XIIIk.

Example 72

Preparation of 2'-Methoxy-2-cyclopropylmethyl-9α-methyl-5-benzyl-9β-hydroxy-6,7-benzomorphan (XVk)

Substitution in the procedure of example 37 for the compound XIIIf used therein of an equimolar quantity of compound XIIIk produces the title compound XVk.

Example 73

Preparation of 2',9β-Dihydroxy-2-cyclopropylmethyl-9α-methyl-5-benzyl-6,7-benzomorphan (XVIk)

Substitution in the procedure of example 20 for the compound XVb used therein of an equimolar quantity of compound XVk produces the title compound XVIk.

Example 74

Resolution of dl-2',9β-Dihydroxy-9α-methyl-5-allyl-2-cyclobutylmethyl-6,7-benzomorphan into its optical isomers A. d-2',9β-Dihydroxy-9α-methyl-5-allyl-2-cyclobutylmethyl-6,7-benzomorphan tartrate (d-XVIc)

A solution of 0.920 g. (6.13 mmole) of d-tartaric acid in 10 ml. of hot methanol was added to 2 g. (6.13 mmole) of dl-2',9β-dihydroxy-9α-methyl-5-allyl-2-cyclobutylmethyl-6,7-benzomorphan. The solution was then concentrated to 5 ml. and to it was added 15 ml. of acetone. Upon standing at 4° for 16 hours, there was obtained 0.70 g. of d-tartaric acid salt; $[\alpha]_D^{22} = +52.5$ (C, 0.5; MeOH). The salt was recrystallized three times:

1. 0.70 g. of the d-tartaric acid salt was dissolved in 3.5 ml. of hot methanol and diluted with 7 ml. of acetone. There was obtained 0.480 g. of the d-tartaric acid salt; $[\alpha]_D^{22} = +64.87$ (C, 0.4; MeOH).

2. 0.480 g. of the d-tartaric acid salt was dissolved in 5 ml. of hot methanol and diluted with 5 ml. of acetone.

There was obtained 0.225 g. of the d-tartaric acid salt; $[\alpha]_D^{22} = +66.50$ (C, 0.4; MeOH).

3. 0.225 g. of the d-tartaric acid salt was dissolved in 2 ml. of hot methanol and diluted with 2 ml. of acetone. There was obtained 0.105 g. of the d-tartaric acid salt; $[\alpha]_D^{22} = 71.08$ (C, 0.65; MeOH) m.p. 195°–196°.

B. l-2',9β-Dihydroxy-9α-methyl-5-allyl-2-cyclobutyl-6,7-benzomorphan tartrate (l-XVIc)

From the mother liquors of the first crystallization of the d-tartaric acid salt, we recovered 1.29 g. (3.94 mmoles) free base enriched in l-isomer. In a same procedure as described for the resolution of the d-isomer, there was obtained 1.0 g. of l-tartaric acid salt. Recrystallization from 5 ml. of methanol and 10 ml. of acetone gave 0.586 g. of the l-tartaric acid salt; $[\alpha]_D^{22} = -69.13$ (C, 0.460; MeOH) m.p. 192°–194°.

Example 75

Preparation of 2',9β-Dihydroxy-2-(2,2-ethanopropyl)-9α-methyl-5-n-propyl-6,7-benzomorphan (XVIm)

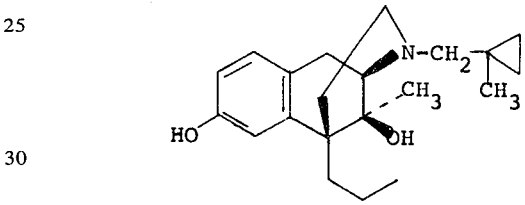

A. 2'-Methoxy-2-(2,2-ethanoethyl-carbonyl)-5-allyl-9β-methyl-9α-hydroxy-6,7-benzomorphan (XIVm)

Substitution in the procedure of example 18 for the cyclopropane carboxylic acid chloride used therein of an equimolar quantity of 2,2-ethanoethylcarboxylic acid chloride produces the title compound XIVm.

B. 2'-Methoxy-2-(2,2-ethanopropyl)-5-allyl-9α-methyl-9β-hydroxy-6,7-benzomorphan (XVm)

Substitution in the procedure of example 19 for the compound XIVb used therein of an equimolar quantity of XIVm produces the title produce XVm.

C. 2'-Methoxy-2-(2,2-ethanopropyl)-5-n-propyl)-9α-methyl-9β-hydroxy-6,7-benzomorphan (XVn)

Substitution in the procedure of example 26 for the compound XVb used therein of an equimolar quantity of XVm produces the title compound XVn.

D. 2',9β-Dihydroxy-2-(2,2-ethanopropyl-9α-methyl-5-n-propyl-6,7-benzomorphan (XVIm)

Substitution in the procedure of example 27 for the compound XVe used therein of an equimolar quantity of XVn produced the title compound XVIm.

Example 76

Preparation of 2',9β-Dihydroxy-2-(2'-methylcyclobutylmethyl-5-allyl-9α-methyl-6,7-benzomorphan (XVIp)

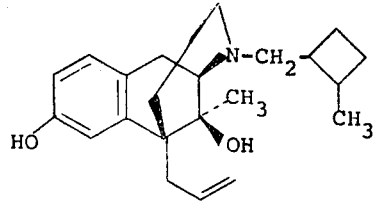

A. 2'-Methoxy-2-(2'-methylcyclobutylcarbonyl)-5-allyl-9α-methyl-9β-hydroxy-6,7-benzomorphan (XIVp)

Substitution in the procedure of example 18 for the cyclopropane carboxylic acid chloride used therein of an equimolar quantity of 2'-methylcyclobutane carboxylic acid chloride produces the title compound XIVp.

B. 2'-methoxy-2-(2'-methylcyclobutylmethyl-5-allyl-9α-methyl-9β-hydroxy-6,7-benzomorphan (XVp)

Substitution in the procedure of example 17 for the compound XIVb used therein of an equimolar quantity of XIVp produces the title produce XVp.

C. 2',9β-Dihydroxy-2-(2'-methyl-cyclobutylmethyl)-5-allyl-9α-methyl-9β-hydroxy-6,7-benzomorphan (XVIp)

Substitution in the procedure of example 27 for the compound XVe used therein of an equimolar quantity of XVn produces the title compound XVIp.

Example 77

Preparation of 2'-acetoxy-2-cyclopropylmethyl-9β-hydroxy-9α-methyl-5-propyl-6,7-benzomorphan (XXXIV)

Equimolar quantities of acetyl chloride, compound XVIe and pyridine are mixed together in dry methylene chloride and the resultant mixture is heated to 60°C. for several hours under a nitrogen atmosphere to produce the title compound.

Example 78

Preparation of 2'-(3'-nicotinoyloxy)-2-cyclopropylmethyl-9β-hydroxy-9α-methyl-5-propyl-6,7-benzomorphan (XXXV)

Equimolar quantitites of 3-nicotinoyl chloride hydrochloride, compound XVIe and pryridine are mixed together in dry methylene chloride and the mixture is heated to 50°C. for 3 hours to produce the title compound.

Example 79

Preparation of 2-cyclopropylmethyl-9β-hydroxy-2'-methoxymethyloxy-9α-methyl-5-propyl-6,7-benzomorphan (XXXVI)

One mole of compound XVIe is placed in 3 liters of benzene. One mole of sodium methoxide is added, followed by the slow addition of 1 mole of chloromethyl ether with stirring. The solution was heated to reflux to yield the title product.

Example 80

Resolution of Compound dl-XVIb into its d and l isomers

A. d - XVIb

A solution of 6.3 g of l-tartaric acid in 35 ml of hot methanol was added to 13.2 g (.042 M) of dl-XVIb. The resulting solution was diluted with 40 ml of acetone and left at room temperature overnight. Upon filtration, there was obtained 8.5 g of the l-tartaric acid salt; $[\alpha]_D^{22} =+ 50.00$ (C, 0.096; MeOH); m.p. 210° - 212°.

The 8.5 g of the l-tartaric acid salt of d-XVIb were dissolved in 150 ml of boiling methanol. The solution was concentrated to 60 ml and left at room temperature for 72 hours to yield 5.6 g of the l-tartaric acid salt of d-XVIb; $[\alpha]_D^{22} =+59.00$ (C, 0.106; MeOH).

A sample was recrystallized 4 times. The free base (d-XVIb) obtained therefrom had an optical rotation of +107.5 ± .5 (C, .200; MeOH).

B. l - XVIb

From the mother liquors of the l-tartaric acid salt preparation, there was recovered 9 g. of free base XVIb enriched in l-isomer. This material was dissolved in 30 ml of methanol and added to a 12 ml methanol solution of 4.3 g of d-tartaric acid and left to stand overnight. Upon filtration, there was obtained 8.2 g of the d-tartaric acid salt of l-XVIb; $[\alpha]_D^{22} - 59.5$.

The 8.2 g of the tartaric acid salt were dissolved in 200 ml. of boiling methanol and then concentrated to 50 ml. Upon standing at room temperature, there was obtained 6.56 g. of the d-tartaric acid salt of l-XVIb; $[\alpha]_D^{22} =-63 \pm 1$ (C, 0.180; MeOH); m.p. 215° - 217°. That sample was sent for elemental analysis.

Anal. Calc'd. for $C_{24}H_{33}NO_8$: C, 62.18; H, 7.17; N, 3.02. Found: C, 62.44; H, 7.35; N, 3.20.

From that sample, the free base was isolated; m.p. 154°–156°; $[\alpha]_D^{22}$ 22— 100.0 ± .5 (C, 0.200; MeOH).

A .500 g sample of the d-tartaric acid salt of l-XVIb from the first recrystallization was recrystallized from 10 ml of methanol to give a sample with $[\alpha]_D^{22}$ - 55.71 (C, 210; MeOH); m.p. 215° - 217°.

That sample was recrystallized once more from MeOH; m.p. 216° - 218°. The free base isolated from this sample of l-XVIb tartrate had an optical rotation of $[\alpha]_D^{22} =-105.48$ (C, 0.164; MeOH).

Example 81

Preparation of l-XVIe from l-XVIb

Two grams of the d-tartaric acid salt of l-XVIb was treated with aqueous 5% sodium carbonate and extracted with ethyl acetate to yield 1.35 g. of free base of l-XVIb; $[\alpha]_D^{22}$ - 100 ± .5 (C, 0.200, MeOH). The free base was dissolved in a sufficient amount of ethanol and hydrogenated at room temperature, 50 p.s.i. over Pd/charcoal 10% for 4 hours. The catalyst was removed by filtration and the solvent evaporated. The residue was recrystallized from a mixture of methanol and water to give 0.780 g of l-XVIe; m.p. 189° - 190° C.; $[\alpha]_D^{22}$ - 120.408 (C, .098; MeOH)

Calc'd. for $C_{20}H_{29}NO_2$: C, 76.14; H, 9.26; N, 4.44. Found: C, 76.03; H, 9.36; N, 4.36.

Example 82

Preparation of l-2', 9β-Dihydroxy-9α-methyl-5-propyl-2-cyclobutyl-6,7-benzomorphan HCl (l-XVIr)

A solution of 2 g. of l-XVIc l-tartaric acid salt, $[\alpha]_D^{22}$ - 69.13, in 100 ml. of alcohol was hydrogenated at 50 p.s.i. of $H_2$ over 0.200 g. of Pd/charcoal 10% for 1 hour. The catalyst was removed by filtration and the solvent evaporated, we thus obtained a hygroscopic residue that could not be crystallized. The l-tartaric acid salt was converted to the hydrochloride salt which crystallized out of acetone to give 1.3 g of l-XVIr HCl. It was recrystallized from a mixture of methanol/ether to a constant m.p. of 216° - 218° C.; $[\alpha]_D^{22}$ - 91.37 (C, 0.394, MeOH).

Calc'd. for $C_{21}H_{31}NO_2 \cdot HCl$: C, 68.92; H, 8.81; N, 3.82. Found: C, 69.12; H, 9.03; N, 3.94.

We claim:

1. A compound having the formula

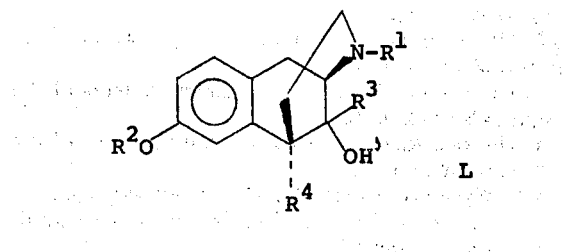

L wherein $R^1$ is selected from the group consisting of

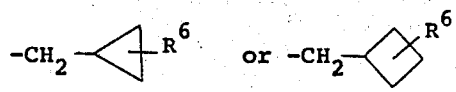

in which $R^6$ is H or $CH_3$, $R^2$ is selected from the group consisting of H, (lower)alkyl, (lower)alkanoyl,

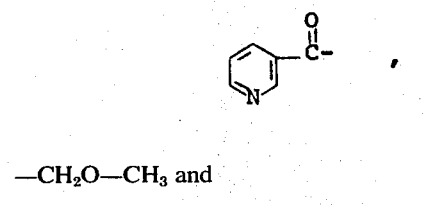

—$CH_2O$—$CH_3$ and

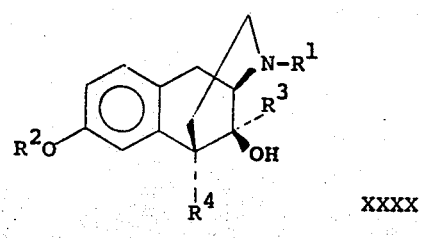

$R^3$ is H or $CH_3$, $R^4$ is n-propyl or (lower)alkenyl; or a pharmaceutically acceptable acid addition salt thereof.

2. A compound of claim 1 having the formula

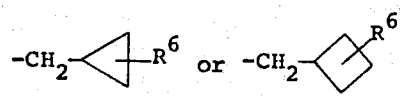

XXXX wherein $R^1$ is selected from the group consisting of

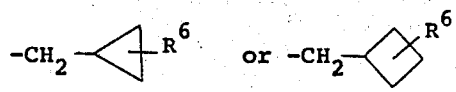

in which $R^6$ is H or $CH_3$, $R^2$ is selected from the group consisting of H, (lower)alkyl, (lower)alkanoyl,

—$CH_2O$—$CH_3$ and

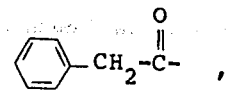

$R^3$ is H or $CH_3$, $R^4$ is n-propyl or (lower)alkenyl; or a pharmaceutically acceptable acid addition salt thereof.

3. A compound of claim 2 wherein $R^1$ is

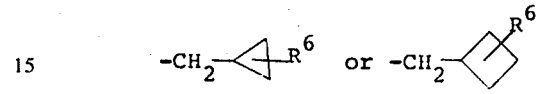

in which $R^6$ is H or $CH_3$, $R^2$ is H, $CH_3$,

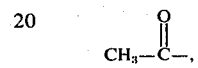

or

and $R^5$ is H, $R^3$ is H or $CH_3$, $R^4$ is n-propyl or (lower)alkenyl; or a pharmaceutically acceptable acid addition salt thereof.

4. A compound of claim 2 wherein $R^1$ is

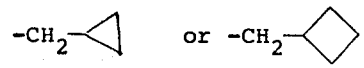

$R^2$ is H, $CH_3$ or

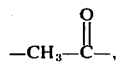

$R^5$ is hydrogen, $R^3$ is methyl or H, $R^4$ is n-propyl or allyl; or a pharmaceutically acceptable acid addition salt thereof.

5. A compound of claim 2 wherein $R^1$ is

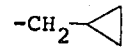

$R^2$ is H, $R^3$ is methyl, $R^4$ is n-propyl or allyl and $R^5$ is H; or the hydrochloride salt thereof.

6. A compound of claim 2 wherein $R^1$ is

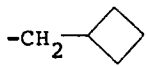

$R^2$ is H, $R^3$ is methyl, $R^4$ is n-propyl or allyl and $R^5$ is H; or the hydrochloride salt thereof.

7. A compound having the formula

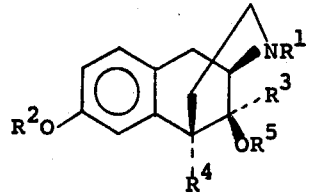

LX wherein R¹ is H, R² is H or (lower)alkyl, R³ is H or methyl, R⁴ is n-propyl or allyl, and R⁵ is H; or an acid addition salt thereof.

8. A compound having the formula

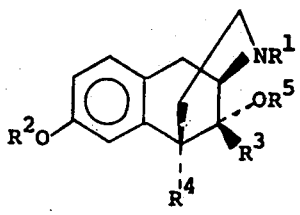

wherein R¹ is H, R² is H or (lower)alkyl, R³ is H or methyl, R⁴ is n-propyl or allyl, and R⁵ is H; or an acid addition salt thereof.

9. A compound of claim 7 wherein R¹ is H, R² is H or methyl, R³ is methyl, R⁴ is n-propyl or allyl and R⁵ is H; or an acid addition salt thereof.

10. The essentially pure levorotatory isomers of the compounds of claim 2.

11. The essentially pure levorotatory isomers of the compounds of claim 3.

12. The essentially pure levorotatory isomers of the compounds of claim 4.

13. The essentially pure levorotatory isomers of the compounds of claim 6.

14. The essentially pure levorotatory isomers of the compound of claim 7.

15. 2-Cyclopropylmethyl-2′,9β-dihydroxy-9α-methyl-5-n-propyl-6,7-benzomorphan; or a pharmaceutically acceptable salt thereof.

16. The tartrate or hydrochloride salt of the compound of claim 15.

17. The essentially pure levorotatory isomer of the compound of claim 15.

* * * * *

UNITED STATES PATENT OFFICE
CERTIFICATE OF CORRECTION

Patent No. 3,966,747            Dated June 29, 1976

Inventor(s)   Ivo Monkovic et al

It is certified that error appears in the above-identified patent and that said Letters Patent are hereby corrected as shown below:

In Claim 1, in the structural formula at line 2, "$OH^5$" should read --$OR^5$--. At the beginning of line 10, insert --$R^5$ is H,--.

In Claim 2, in the structural formula at line 2, "OH" should read --$OR^5$--. At the beginning of line 10, insert --$R^5$ is H,--.

Signed and Sealed this

Second Day of November 1976

[SEAL]

*Attest:*

RUTH C. MASON
*Attesting Officer*

C. MARSHALL DANN
*Commissioner of Patents and Trademarks*